United States Patent
Whitesides et al.

(10) Patent No.: US 12,288,584 B2
(45) Date of Patent: Apr. 29, 2025

(54) STORAGE OF INFORMATION USING MIXTURES OF MOLECULES

(71) Applicants: President and Fellows of Harvard College, Cambridge, MA (US); Northwestern University, Evanston, IL (US)

(72) Inventors: George M. Whitesides, Newton, MA (US); Brian J. Cafferty, Cambridge, MA (US); Alexei S. Ten, Evanston, IL (US); Michael J. Fink, Cambridge, MA (US); Daniel J. Preston, Cambridge, MA (US); Milan M. Mrksich, Hinsdale, IL (US); Amit A. Nagarkar, Cambridge, MA (US)

(73) Assignees: President and Fellows of Harvard College, Cambridge, MA (US); Northwestern University, Evanston, IL (US)

( * ) Notice: Subject to any disclaimer, the term of this patent is extended or adjusted under 35 U.S.C. 154(b) by 860 days.

(21) Appl. No.: 17/214,664

(22) Filed: Mar. 26, 2021

(65) Prior Publication Data

US 2021/0217474 A1    Jul. 15, 2021

Related U.S. Application Data

(63) Continuation of application No. PCT/US2019/053521, filed on Sep. 27, 2019.
(Continued)

(51) Int. Cl.
*G11C 13/02* (2006.01)
*B82B 1/00* (2006.01)
*B82B 3/00* (2006.01)

(52) U.S. Cl.
CPC .............. *G11C 13/02* (2013.01); *B82B 1/008* (2013.01); *B82B 3/0019* (2013.01); *B82B 3/0047* (2013.01); *B82B 3/009* (2013.01)

(58) Field of Classification Search
CPC ........ G11C 13/02; G11B 7/1353; B82Y 30/00
See application file for complete search history.

(56) References Cited

U.S. PATENT DOCUMENTS 5,453,970 A * 9/1995 Rust ...................... B82Y 30/00
                                                              369/126
5,961,923 A    10/1999 Nova et al.
(Continued)

FOREIGN PATENT DOCUMENTS

WO    WO-96/036436 A1    11/1996
WO    WO-97/007440 A1    2/1997
(Continued)

OTHER PUBLICATIONS

Aksakal et al., "Applications of Discrete Synthetic Macromolecules in Life and Materials Science: Recent and Future Trends" Advanced Science, vol. 8, 22 pages (2021).
(Continued)

*Primary Examiner* — Lam S Nguyen
(74) *Attorney, Agent, or Firm* — Alexander Akhiezer; Erik Huestis; Foley Hoag LLP

(57) ABSTRACT

A machine-readable medium and methods of reading and writing same are disclosed. The machine-readable medium comprises a substrate having an array of addressable locations thereon, each addressable location adapted to be physically associated with a collection of non-polymeric molecules. The molecules in each collection are selected from a set of unambiguously identifiable molecules, each molecule uniquely associated with a predetermined position in a numerical value, wherein the presence of the molecule in the collection indicates a predetermined digit at the associated
(Continued)

position and the absence of said molecule in the collection indicates a zero at said associated position.

14 Claims, 21 Drawing Sheets

Specification includes a Sequence Listing.

Related U.S. Application Data

(60) Provisional application No. 62/846,367, filed on May 10, 2019, provisional application No. 62/738,792, filed on Sep. 28, 2018.

(56) References Cited

U.S. PATENT DOCUMENTS

| | | | |
|---|---|---|---|
| 6,052,354 | A | 4/2000 | Gudesen et al. |
| 6,589,726 | B1 | 7/2003 | Butler et al. |
| 7,470,518 | B2 | 12/2008 | Chiu et al. |
| 9,013,968 | B2 | 4/2015 | Monzar |
| 9,384,320 | B2 | 7/2016 | Church |
| 9,582,771 | B2 | 2/2017 | Perez-Mercader et al. |
| 9,928,869 | B2 | 3/2018 | Church |
| 10,650,312 | B2 | 5/2020 | Roquet et al. |
| 10,838,939 | B2 | 11/2020 | Walder et al. |
| 10,917,109 | B1 | 2/2021 | Dimopoulou et al. |
| 11,093,865 | B2 | 8/2021 | Rubenstein et al. |
| 11,106,633 | B2 | 8/2021 | Sagi et al. |
| 11,302,421 | B2 | 4/2022 | Yao et al. |
| 11,514,331 | B2 | 11/2022 | Bathe et al. |
| 11,535,842 | B2 | 12/2022 | Roquet et al. |
| 2002/0102559 | A1 | 8/2002 | Cattell |
| 2003/0064532 | A1 | 4/2003 | Chen |
| 2004/0114491 | A1* | 6/2004 | Psaltis .................. G11B 7/1353 |
| 2004/0185169 | A1 | 9/2004 | Peck et al. |
| 2005/0162895 | A1 | 7/2005 | Kuhr et al. |
| 2006/0110819 | A1 | 5/2006 | Lomas et al. |
| 2006/0191319 | A1 | 8/2006 | Kurup |
| 2007/0072193 | A1 | 3/2007 | Shah |
| 2014/0200716 | A1 | 7/2014 | Perez-Mercader et al. |
| 2018/0121478 | A1 | 5/2018 | Walder et al. |
| 2018/0137418 | A1 | 5/2018 | Roquet et al. |
| 2019/0072493 | A1 | 3/2019 | Wang et al. |
| 2019/0121936 | A1 | 4/2019 | Church |
| 2019/0162714 | A1 | 5/2019 | Karimi |
| 2022/0012646 | A1 | 1/2022 | Rubenstein et al. |
| 2022/0180083 | A1 | 6/2022 | Whitesides et al. |
| 2022/0301624 | A1 | 9/2022 | Whitesides et al. |
| 2023/0027270 | A1 | 1/2023 | Rubenstein et al. |

FOREIGN PATENT DOCUMENTS

| | | |
|---|---|---|
| WO | WO-2007/128804 A2 | 11/2007 |
| WO | WO-2008/091378 A2 | 7/2008 |
| WO | WO-2014/014991 A2 | 1/2014 |
| WO | WO-2016/205156 A1 | 12/2016 |
| WO | WO-2017/011492 A1 | 1/2017 |
| WO | WO-2018/081566 A1 | 5/2018 |
| WO | WO-2018/094108 A1 | 5/2018 |
| WO | WO-2018/094115 A1 | 5/2018 |
| WO | WO-2019/246434 A1 | 12/2019 |
| WO | WO-2020/112233 A9 | 9/2020 |
| WO | WO-2021/041667 A1 | 3/2021 |
| WO | WO-2021/062220 A1 | 4/2021 |
| WO | WO-2022/069022 A1 | 4/2022 |
| WO | WO-2024/027620 A1 | 2/2024 |

OTHER PUBLICATIONS

Arcadia et al. "Multicomponent molecular memory" Nature Communications, vol. 11, Issue 691: 8 pages (2020).
Arita et al., "DNA Memory" Handbook of Natural Computing, pp. 1281-1318 (2012).
Banda et al., "Online learning in a chemical perceptron," Artificial Life, 19: 195-219 (2013).
Bohn et al., "Molecular data storage with zero synthetic effort and simple read-out" Scientific Reports, vol. 12, 8 pages (2022).
Boukis et al., "Multicomponent reactions provide key molecules for secret communication" Nature Communications, vol. 9, 9 pages (2018).
Hjelmfelt et al., "Chemical implementation of neural networks and Turing machines," Proceedings of the National Academy of Sciences, 88: 10983-10987 (1991).
International Search Report and Written Opinion for International Application No. PCT/US19/38301 dated Nov. 27, 2019.
International Search Report and Written Opinion for International Application No. PCT/US20/52814 dated Jan. 19, 2021.
Kennedy et al., "Encoding information in synthetic metabolomes," PLoS One, 14(7): e0217364 (12 pages) (2019).
Niu et al., "Enzyme-Free Translation of DNA into Sequence-Defined Synthetic Polymers Structurally Unrelated to Nucleic Acids" Nat Chem, 5(4): 282-292 (2013).
Rose et al., "Computing chemicals: Perceptions using mixtures of small molecules," 2018 IEEE International Symposium on Information Theory (ISIT), retrieved online <https://ieeexplore.ieee.org/abstract/document/8437814>: 2236-2240 (2018).
Tabatabei., "Next Generation DNA-Based Data Recorders" University of Illinois Urbana-Champaign (2022).
Tsaftaris et al., "On Designing DNA Databases for the Storage and Retrieval of Digital Signals" LNCS, vol. 3611, pp. 1192-1201 (2005).
Yu et al., "Small-Molecule-Based Organic Field-Effect Transistor for Nonvolatile Memory and Artificial Synapse" Advanced Functional Materials, vol. 29, Issue 50 (2019).
Arcadia et al., "Parallelized Linear Classification with Volumetric Chemical Perceptrons," Brown University, 1-9 (2018).
Cafferty et al., "Storage of Information Using Small Organic Molecules," ACS Cent. Sci, 5:911-916 (2019).
Gurard-Levin et al., "Peptide Arrays Identify Isoform-Selective Substrates for Profiling Endogenous Lysine Deacetylase Activity," ACS Chemical Biology, 5(9):863-873 (2010).
International Search Report and Written Opinion for International Application No. PCT/US2019/053521 mailed Jul. 28, 2020.
International Search Report and Written Opinion for International Application No. PCT/US2020/048190 dated Nov. 2, 2020.
Kornacki et al., "Acetyltransferase p300/CBP Associated Factor (PCAF) Regulates Crosstalk-Dependent Acetylation of Histone H3 by Distal Site Recognition," ACS Chem. Biol., 10:157-164 (2015).
Martens et al., "Multifunctional sequence-defined macromolecules for chemical data storage," Nature Communications, 9(4451):1-8 (2018).
O'Kane et al., "An Assay Based on SAMDI Mass Spectrometry for Profiling Protein Interaction Domains," Journal of The American Chemical Society, 139:10320-10327 (2017).
Riepl et al., "Electrical Control of Alkanethiols Self-Assembly on a Gold Surface as an Approach for Preparation of Microelectrode Arrays," Mikrochimica Acta, 131(1): 29-34 (1999).
Rosenstein et al., "Principles of Information Storage in Small-Molecule Mixtures," arxiv.org, Cornell University Library, 201 Olin Library Cornell University Ithaca, NY 14853 (2019).
Szymczak et al., "Peptide Arrays: Development and Application," Anal. Chem., 90:266-282 (2018).
Szymczak et al., "Using Peptide Arrays To Discover the Sequence-Specific Acetylation of the Histidine-Tyrosine Dyad," Biochemistry, 58:1810-1817 (2019).

* cited by examiner

Correspondence of an alphanumeric character (the letter "K") encoded in ASCII in binary, and in four molbits as oligopeptides.

| Byte | Letter | | | | K | | | | |
|---|---|---|---|---|---|---|---|---|---|
| | Binary String in ASCII | 0 | 1 | 0 | 0 | 1 | 0 | 1 | 1 |
| | Molbit Assignment to Binary String | | Ac-ZK(me3)C | | | Ac-GVK(me3)C | | Ac-ALK(me3)C | Ac-GFK(me3)C |
| | Oligopeptide Number* | | | | | | | | |
| I | | — | 2 | — | — | 5 | — | 7 | 8 |
| II | | — | 10 | — | — | 13 | — | 15 | 16 |
| III | | — | 18 | — | — | 21 | — | 23 | 24 |
| IV | | — | 26 | — | — | 29 | — | 31 | 32 |

Ac: acetyl, A: alanine, G: glycine, C: cysteine, F: phenylalanine, K(me3): Nε,Nε,Nε-trimethyl lysine, L: leucine, V: valine, Z: 2-aminobutyric acid. See Supplementary Information Table 1 for binary assignment of printable character in ASCII.
*Numbering scheme for the 32 peptides used in this work (Extended Data Table 1 gives complete structures).

Fig. 1

Assignment of 32 peptides to 32 molbits (4 molbytes) by ascending mass-to-charge ratio.

| Molbyte Number | Molbit Number | Oligopeptide Number | sequence | m.w. (g mol⁻¹) | m/z obs.* (a.m.u.) |
|---|---|---|---|---|---|
| I | 1 | 1 | Ac-AK(me3)C | 404 | 1255 |
|   | 2 | 2 | Ac-(abu)K(me3)C | 418 | 1269 |
|   | 3 | 3 | Ac-VK(me3)C | 432 | 1283 |
|   | 4 | 4 | Ac-GGK(me3)C | 447 | 1298 |
|   | 5 | 5 | Ac-GVK(me3)C | 489 | 1340 |
|   | 6 | 6 | Ac-GLK(me3)C | 503 | 1354 |
|   | 7 | 7 | Ac-ALK(me3)C | 517 | 1368 |
|   | 8 | 8 | Ac-GFK(me3)C | 537 | 1388 |
| II | 1 | 9 | Ac-GVGK(me3)C | 546 | 1397 |
|   | 2 | 10 | Ac-GLGK(me3)C | 560 | 1411 |
|   | 3 | 11 | Ac-GAGGK(me3)C | 575 | 1426 |
|   | 4 | 12 | Ac-GL(abu)K(me3)C | 588 | 1439 |
|   | 5 | 13 | Ac-GFGK(me3)C | 594 | 1445 |
|   | 6 | 14 | Ac-GRGK(me3)C | 603 | 1454 |
|   | 7 | 15 | Ac-GPAGK(me3)C | 615 | 1466 |
|   | 8 | 16 | Ac-AYGK(me3)C | 624 | 1475 |
| III | 1 | 17 | Ac-GPFK(me3)C | 634 | 1485 |
|   | 2 | 18 | Ac-GVVGK(me3)C | 645 | 1496 |
|   | 3 | 19 | Ac-G(abu)FGK(me3)C | 679 | 1530 |
|   | 4 | 20 | Ac-GVFGK(me3)C | 693 | 1544 |
|   | 5 | 21 | Ac-GVYGK(me3)C | 709 | 1560 |
|   | 6 | 22 | Ac-GARGGK(me3)C | 731 | 1582 |
|   | 7 | 23 | Ac-GAVV(abu)K(me3)C | 744 | 1595 |
|   | 8 | 24 | Ac-GFYGK(me3)C | 757 | 1608 |
| IV | 1 | 25 | Ac-GYYGK(me3)C | 773 | 1624 |
|   | 2 | 26 | Ac-GYYAK(me3)C | 787 | 1638 |
|   | 3 | 27 | Ac-GPYFK(me3)C | 797 | 1648 |
|   | 4 | 28 | Ac-GRGFGK(me3)C | 807 | 1658 |
|   | 5 | 29 | Ac-GYFGGK(me3)C | 814 | 1665 |
|   | 6 | 30 | Ac-GYYGGK(me3)C | 830 | 1681 |
|   | 7 | 31 | Ac-AYYGGK(me3)C | 844 | 1695 |
|   | 8 | 32 | Ac-GYY(abu)GK(me3)C | 858 | 1709 |

Ac: acetyl, Abu: 2-aminobutyric acid, A: alanine, G: glycine, C: cysteine, F: phenylalanine, K(me3): N$^\varepsilon$,N$^\varepsilon$,N$^\varepsilon$-trimethyl lysine L: leucine, P: proline, R: arginine, V: valine, Y: tyrosine, a.m.u.: atomic mass unit.

*The observed mass-to-charge ratio (m/z) includes the oligopeptide plus the mixed disulfide derived from the SAM, which is formed during laser-assisted desorption/ionization (+ 851 a.m.u.).

Liberty of 32 peptides (MolBits)
32 bits = 4 bytes
information cap  charge  anchor 1-5 amino acids
Z Abu   A Ala   R Arg
G Gly   L Leu   F Phe
P Pro   Y Tyr   V Val Δm/z
6-42 a.m.u.

Fig. 3B

Molbit ①
Molbit ②

Fig. 3C

Byte I: A, Z, V, GG, GV, GL, AL, GF, GVG, GLG, GAGG
Byte II: GFG, GRG, GPAG, AYG, GPP, GVVG
Byte III: GZFG, GVFG, GVYG, GARGG, GAVYZ, GFYG
Byte IV: GVYG, GYYA, GPYF, GRGFG, GYFGG, GVYGG, AVYGG, GYYZG

STORAGE OF INFORMATION USING MIXTURES OF MOLECULES

RELATED APPLICATIONS

This application is a continuation of International Application No. PCT/US2019/053521, filed Sep. 27, 2019, which claims the benefit of U.S. Provisional Application No. 62/738,792, filed on Sep. 28, 2018, and U.S. Provisional Application No. 62/846,367, filed on May 10, 2019. The entire teachings of the above application are incorporated herein by reference.

GOVERNMENT SUPPORT

This invention was made with government support under W911NF-18-2-0030 awarded by the U.S. Army/Army Research Office. The government has certain rights in the invention.

BACKGROUND OF THE INVENTION

Although information and information technology are ubiquitous, its very ubiquity has posed new types of problems. Three that involve storage of information (rather than computation) include its usage of energy, the robustness of stored information over long times, and its ability to resist corruption through hacking. The difficulty in solving these problems using existing storage method has stimulated interest in the possibilities available through fundamentally different strategies, including storage of information in molecules.

Technologies from printing with ink on paper, to very sophisticated electronic, optical, and magnetic methods, are used to store information. The importance (across a range of parameters: cost, space, energy use, rate of reading and writing, rate of degradation on storage, potential for corruption through hacking, independence of protocols and hardware for reading) is such that each of these methods has weaknesses in addition to its strengths, and there remains a need to evaluate possible alternatives. New methods of information storage would circumvent some of the weaknesses of the existing technologies, and perhaps open new applications.

SUMMARY OF THE INVENTION

In an example embodiment, the present invention is a machine-readable medium comprising a substrate having an array of addressable locations thereon, each addressable location adapted to be physically associated with a collection of non-polymeric molecules. The molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position. It will be understood by a person or ordinary skill in the art that, in an alternative embodiment, it is the presence of a molecule that may indicate a zero at an associated position, while the absence of a molecule may indicate a predetermined non-zero digit.

In another example embodiment, the present invention is a machine-readable medium comprising a substrate having an array of addressable locations thereon, each addressable location adapted to be physically associated with a collection of molecules. Each molecule in the collection is a sequence-independent polymer, and the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position. It will be understood by a person or ordinary skill in the art that, in an alternative embodiment, it is the presence of a molecule that may indicate a zero at an associated position, while the absence of a molecule may indicate a predetermined non-zero digit.

In another example embodiment, the present invention is a method of writing data to a machine-readable medium. The method comprises receiving a binary value comprising a plurality of bits, each bit having a position; receiving a one-to-one association between a plurality of bit positions and a set of unambiguously identifiable molecules; determining a collection of molecules corresponding to the binary value, wherein determining the collection comprises: including in the collection the molecule associated with each position in which the bit has a value of 1; and omitting the molecule associated with each position in which the bit has a value of 0; linking the molecules of the collection with a substrate of the machine-readable medium at an addressable location thereon. It will be understood by a person of ordinary skill in the art that, in an alternative embodiment, the molecule can be omitted if the bit value is 1, and included if the bit value is 0.

In another example embodiment, the present invention is a method of reading data from a machine-readable medium. The method comprises receiving a one-to-one association between each of a plurality of bit positions and a set of unambiguously identifiable molecules; determining a collection of molecules physically associated with a substrate of the machine-readable medium at an addressable location thereon; determining a binary value from the collection of molecules, wherein determining the binary value comprises: setting to 1 the bit at the position in the binary value for which its associated molecule is present in the collection and setting to 0 each bit at the position of the binary value for which its associated molecule is not present in the collection. It will be understood by a person or ordinary skill in the art that, in an alternative embodiment, the bit is set to 1 if a molecule is absent and the bit is set to 0 if the molecule is present.

In another example embodiment, the present invention is a method of writing data to a machine-readable medium. The method comprises receiving a numerical value comprising a plurality of digits, each digit having a position; receiving a one-to-one association between a plurality of digit/position pairs and a set of unambiguously identifiable molecules; determining a collection of molecules corresponding to the numerical value, wherein determining the collection comprises: including in the collection the molecule associated with each position having the associated digit in the numerical value; linking the molecules of the collection with a substrate of the machine-readable medium at an addressable location thereon. It will be understood by a person or ordinary skill in the art that, in an alternative embodiment, the molecule is omitted if the bit value is 1, and included if the bit value is 0.

In another example embodiment, the present invention comprises a method of reading data from a machine-readable medium. The method comprises receiving a one-to-one association between a plurality of digit/position pairs and a set of unambiguously identifiable molecules; determining a collection of molecules physically associated with a substrate of the machine-readable medium at an addressable location thereon; determining a numerical value from the collection of molecules, wherein determining the numerical value comprises: setting each position of the numerical value to the digit whose associated molecule is present in the collection. It will be understood by a person or ordinary skill in the art that, in an alternative embodiment, the bit is set to 1 if a molecule is absent and the bit is set to 0 if the molecule is present.

The present invention advantageous provides for an archival, long-term storage of information, which is tamper-resilient and requires no or low energy storage devices. The invention described herein is capable of long-term (over 100 years), power-free, WORM (write-once-read-many) storage of information, which is not possible with currently available electronic, magnetic, or optical storage media. It can be engineered to achieve useful writing and reading rates for both archival purposes and product labeling (authentication, barcoding). Other molecular approaches, which use sequence-dependent polymeric molecules (e.g., DNA), are many orders of magnitude slower.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 presents a table that summarizes the strategy for encoding the letter "K" using polypeptides according to an example embodiment of the present invention.

FIG. 2 presents a table that summarizes a complete assignment of oligopeptides sufficient to encode four bytes in a single mixture, with their assignments to a binary molecular representation according to an example embodiment of the present invention.

FIG. 3A is an illustration of oligopeptide molbits, according to example embodiment of the present invention, the oligopeptides containing various regions.

FIG. 3B is a schematic diagram showing an example of two immobilized oligopeptides according to an example embodiment of the present invention.

FIG. 3C shows a spectrum of a SAMDI spot containing 32 molbits encoded by polypeptides according to an example embodiment of the present invention.

DETAILED DESCRIPTION OF THE INVENTION

Figure 4:
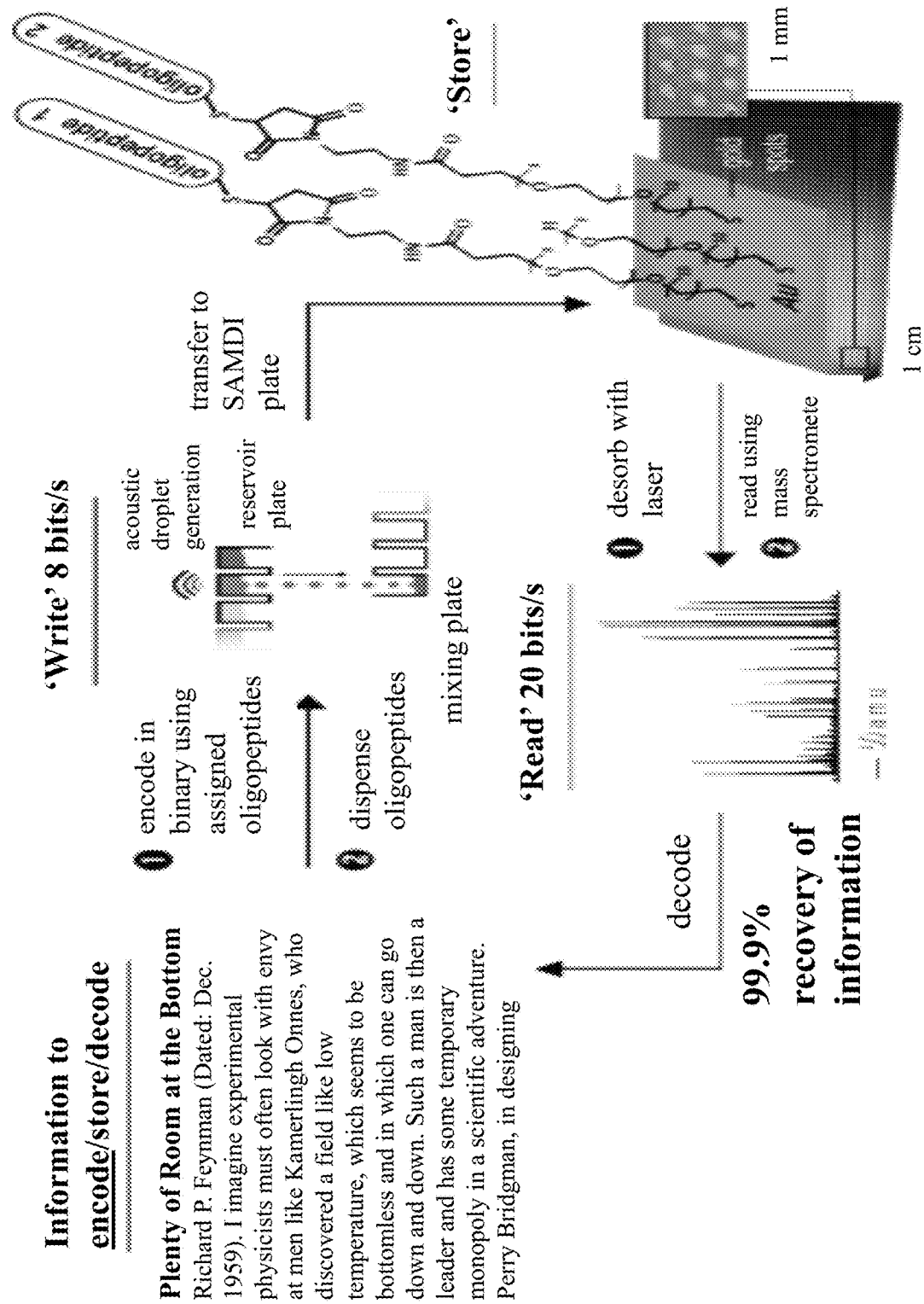
FIG. 4 is a schematic diagram of the process that can be used to 'write', 'store' and 'read' text using the set of 32 peptides described herein as an example embodiment of the present invention.

A description of example embodiments of the invention follows.

The present invention addresses the difficulties in lowering energy usage for information storage, improving the robustness of stored information over long times, and the ability of the stored information to resist corruption through hacking including storage of information in molecules. Disclosed herein are devices and methods that can store information in mixtures of readily available, stable molecules. The disclosed methods use a common, small set of molecules, also referred to as libraries, (in one example embodiment, a library of eight to thirty-two oligopeptides, in another example embodiment, a library of small molecules having molecular weight of, for example, less than or equal to about 1,500 Da) to write information (in one example embodiment, binary information). The disclosed methods minimize the time and difficulty of synthesis of new molecules. It also circumvents the challenges of encoding and reading messages in linear sequence-dependent macromolecules (e.g., DNA). In one example embodiment, a total of approximately 400 kilobits (both text and images) have been encoded, written, stored, and read as mixtures of molecules, with greater than 99% recovery of information, written at an average rate of 8 bits/s, and read at a rate of 20 bits/s.

In a first example embodiment, the present invention is a machine-readable medium comprising: a substrate having an array of addressable locations thereon, each addressable location adapted to be physically associated with a collection of non-polymeric molecules, wherein the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position.

It will be understood by a person of ordinary skill in the art that in an alternative embodiment, it is the presence of a molecule that may indicate a zero at an associated position, while the absence of a molecule may indicate a predetermined non-zero digit.

In a second example embodiment, the present invention is a machine-readable medium comprising: a substrate having an array of addressable locations thereon, each addressable location adapted to be physically associated with a collection of molecules, wherein each molecule in the collection is a sequence-independent polymer, and wherein the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position.

It will be understood by a person of ordinary skill in the art that in an alternative embodiment, it is the presence of a molecule that may indicate a zero at an associated position, while the absence of a molecule may indicate a predetermined non-zero digit.

Definitions

The nomenclature used to define the peptides is that typically used in the art wherein the amino group at the N-terminus appears to the left and the carboxyl group at the C-terminus appears to the right.

The term "amino acid" includes both a naturally occurring amino acid and a non-natural amino acid. The term "amino acid," unless otherwise indicated, includes both isolated amino acid molecules (i.e. molecules that include both, an amino-attached hydrogen and a carbonyl carbon-attached hydroxyl) and residues of amino acids (i.e. molecules in which either one or both an amino-attached hydrogen or a carbonyl carbon-attached hydroxyl are removed). The amino group can be alpha-amino group, beta-amino group, etc. For example, the term "amino acid alanine" can refer either to an isolated alanine H-Ala-OH or to any one of the alanine residues H-Ala-, -Ala-OH, or -Ala-. Unless otherwise indicated, all amino acids found in the compounds described herein can be either in D or L configuration. The term "amino acid" includes salts thereof. Any amino acid can be protected or unprotected. Protecting groups can be attached to an amino group (for example alpha-amino group), the backbone carboxyl group, or any functionality of the side chain. As an example, phenylalanine protected by a benzyloxycarbonyl group (Z) on the alpha-amino group would be represented as Z-Phe-OH.

As used herein, the term "oligopeptide" refers to two or more amino acids covalently linked by at least one amide bond (i.e. a bond between an amino group of one amino acid and a carboxyl group of another amino acid selected from the amino acids of the peptide fragment).

As used herein, "physically associated" means localized to or contained within a location. The molecules may be physically associated with the substrate by being linked (i.e., covalently or non-covalently bonded) to it, or chemically/physically adsorbed to the substrate, or be present in a solution which is contained within an addressable location on the substrate, such as in a well of a multi-well plate.

As used herein, the term "linked" means covalently or non-covalently bonded.

As used herein, the term "sequence-independent polymer" refers to a polymer that is unambiguously identifiable, as defined herein, and wherein permutations of the order of monomer residues of such polymer does not affect the property of being unambiguously identifiable. The term "sequence-independent polymer" includes molecules that comprise a moiety that is a sequence-independent polymer.

As used herein, the term "unambiguously identifiable," when referring to a molecule, means being uniquely identifiable within a collection that includes such molecule.

As used herein a "physical property" refers to a readable output by which each molecule in a collection of molecules can be identified using physico-chemical techniques. Example of readable outputs include spectroscopic signals (e.g., mass spectroscopy, nuclear magnetic resonance (NMR), Raman spectroscopy, fluorescence spectroscopy, absorbance spectroscopy (ultra violet (UV), visible, near-infra red (NIR), infrared (IR)), X-ray photoelectron spectroscopy (XPS), UV photoelectron spectroscopy (UPS), X-ray fluorescence (XRF) spectroscopy), phase transitions (e.g., volatility) detection, and properties that affect electrophoretic or chromatographic mobility (volatility, polarity, mass, partitioning coefficient, hydrophobicity, size of the molecule, ion pairing, electrochemical potentials (e.g., solution pH and charge), molecular structure, and local dipole moment, as well as differential scanning calorimetry and acoustic methods.

As used herein, a "amide" or an "amide bond" refers to a bivalent moiety represented by the structural formula —NR*—C(O)—, where R* is hydrogen or an alkyl, as defined above.

As used herein, an "epoxy resin" refers to any polymer of epoxides that can themselves include an epoxy functional group,

Example Embodiments

In a first aspect of the first and second example embodiments, each molecule of the set of unambiguously identifiable molecules is associated with a binary digit.

In a second aspect of the first and second example embodiments, the numerical value has a radix and a predetermined number of positions. For example, the numerical value is a binary value having a predetermined number, N, of bits. The number N, for example, can be 32. In one example of the third aspect of the first and second example embodiments, each collection encodes a bit string, such as an ASCII value.

In another example, the radix is eight, which is referred to as octal. In another example, the radix is ten, which is referred to as decimal. In another example, the radix is twelve, which is referred to as duodecimal. In another example, the radix is sixteen, which is referred to as hexadecimal. In another example, the radix is twenty, which is referred to as vigesimal. In another example, the radix is sixty, which is referred to as sexagesimal. It will be appreciated that the present disclosure is applicable to arbitrary radices and an arbitrary number of positions in a numerical value.

In a third aspect of the first and second example embodiments, each molecule in the set is identifiable by a physical property.

In an example embodiment of the fourth aspect of the first and second example embodiments, the physical property is a mass-to-charge ratio.

In a fourth aspect of the first and second example embodiments, each molecule in the collection is linked to the substrate at the respective addressable location.

In one aspect of the first example embodiment, each non-polymeric molecule is a small molecule.

In a fifth aspect of the second example embodiment, each molecule in the set is a polymer or an oligomer. For example, each molecule is an oligopeptide. For example, each molecule includes a $N^\varepsilon, N^\varepsilon, N^\varepsilon$-trimethyl lysine-cysteine ($K^{(Me3)}C$) dipeptide at its C-terminus.

In a sixth aspect of the second example embodiment, the numerical value is a binary value having 32 bits; and the set of molecules includes the oligopeptides represented by the following amino acid sequences: Ac-AK(me3)C, Ac-(abu)

K(me3)C, Ac-VK(me3)C, Ac-GGK(me3)C (SEQ ID NO: 1), Ac-GVK(me3)C (SEQ ID NO: 2), Ac-GLK(me3)C (SEQ ID NO: 3), Ac-ALK(me3)C (SEQ ID NO: 4), Ac-GFK(me3)C (SEQ ID NO: 5), Ac-GVGK(me3)C (SEQ ID NO: 6), Ac-GLGK(me3)C (SEQ ID NO: 7), Ac-GAGGK(me3)C (SEQ ID NO: 8), Ac-GL(abu)K(me3)C (SEQ ID NO: 9), Ac-GFGK(me3)C (SEQ ID NO: 10), Ac-GRGK(me3)C (SEQ ID NO: 11), Ac-GPAGK(me3)C (SEQ ID NO: 12), Ac-AYGK(me3)C (SEQ ID NO: 13), Ac-GPFK(me3)C (SEQ ID NO: 14), Ac-GVVGK(me3)C (SEQ ID NO: 15), Ac-G(abu)FGK(me3)C (SEQ ID NO: 16), Ac-GVFGK(me3)C (SEQ ID NO: 17), Ac-GVYGK(me3)C (SEQ ID NO: 18), Ac-GARGGK(me3)C (SEQ ID NO: 19), Ac-GAVV(abu)K(me3)C (SEQ ID NO: 20), Ac-GFYGK(me3)C (SEQ ID NO: 21), Ac-GYYGK(me3)C (SEQ ID NO: 22), Ac-GYYAK(me3)C (SEQ ID NO: 23), Ac-GPYFK(me3)C (SEQ ID NO: 24), Ac-GRGFGK(me3)C (SEQ ID NO: 25), Ac-GYFGGK(me3)C (SEQ ID NO: 26), Ac-GYYGGK(me3)C (SEQ ID NO: 27), Ac-AYYGGK(me3)C (SEQ ID NO: 28), and Ac-GYY(abu)GK(me3)C (SEQ ID NO: 29), wherein each Ac is an acetyl and each Abu is a 2-aminobutyric acid.

In a third example embodiment, the present invention is a method of writing data to a machine-readable medium. The method comprises receiving a binary value comprising a plurality of bits, each bit having a position; receiving a one-to-one association between a plurality of bit positions and a set of unambiguously identifiable molecules; determining a collection of molecules corresponding to the binary value, wherein determining the collection comprises: including in the collection the molecule associated with each position in which the bit has a value of 1; and omitting the molecule associated with each position in which the bit has a value of 0; physically associating the molecules of the collection with a substrate of the machine-readable medium at an addressable location thereon. It is understood by a person of ordinary skill in the art that, in an alternative embodiment, the molecule is omitted if the bit value is 1, and included if the bit value is 0.

In a fourth example embodiment, the present invention is a method of reading data from a machine-readable medium. The method comprises receiving a one-to-one association between each of a plurality of bit positions and a set of unambiguously identifiable molecules; determining a collection of molecules physically associated to a substrate of the machine-readable medium at an addressable location thereon; determining a binary value from the collection of molecules, wherein determining the binary value comprises: setting to 1 the bit at the position in the binary value for which its associated molecule is present in the collection and setting to 0 each bit at the position of the binary value for which its associated molecule is not present in the collection. It is understood by a person of ordinary skill in the art that, in an alternative embodiment, the bit is set to 1 if a molecule is absent and the bit is set to 0 if the molecule is present.

In a fifth example embodiment, the present invention is a method of writing data to a machine-readable medium. The method comprises receiving a numerical value comprising a plurality of digits, each digit having a position; receiving a one-to-one association between a plurality of digit/position pairs and a set of unambiguously identifiable molecules; determining a collection of molecules corresponding to the numerical value, wherein determining the collection comprises: including in the collection the molecule associated with each position having the associated digit in the numerical value; physically associating the molecules of the collection with a substrate of the machine-readable medium at an addressable location thereon. It is understood by a person of ordinary skill in the art that, in an alternative embodiment, the molecule is omitted if the bit value is 1, and included if the bit value is 0.

In a sixth example embodiment, the present invention is a method of reading data from a machine-readable medium. The method comprises receiving a one-to-one association between a plurality of digit/position pairs and a set of unambiguously identifiable molecules; determining a collection of molecules physically associated with a substrate of the machine-readable medium at an addressable location thereon; determining a numerical value from the collection of molecules, wherein determining the numerical value comprises: setting each position of the numerical value to the digit whose associated molecule is present in the collection. It is understood by a person of ordinary skill in the art that, in an alternative embodiment, the bit is set to 1 if a molecule is absent and the bit is set to 0 if the molecule is present.

In a first aspect of the third through sixth example embodiments, receiving the association comprises reading a lookup table.

In a second aspect of the third through sixth example embodiments, the numerical value is a binary value having a predetermined number, N, of bits. For example, the number N can be 32.

In a third aspect of the third through sixth example embodiments, each collection encodes a bit string. A bit string can encode, for example, an ASCII value.

In a fourth aspect of the third through sixth example embodiments, each molecule in the set is identifiable by a physical property. For example, each molecule in the set is identifiable by a mass-to-charge ratio.

In a fifth aspect of the third through sixth example embodiments, each molecule in the collection is linked to the substrate at the respective addressable location.

In a sixth aspect of the fourth or the sixth example embodiments, determining the collection of molecules comprises determining a physical property of the molecules in the collection.

In a seventh aspect of the fourth or the sixth example embodiments, determining the collection of molecules comprises determining the mass-to-charge ratio of the molecules in the collection.

In one aspect of the third through sixth example embodiments, the numerical value is a binary value having 32 bits; and the set of molecules includes the oligopeptides represented by the following amino acid sequences: Ac-AK(me3)C, Ac-(abu)K(me3)C, Ac-VK(me3)C, Ac-GGK(me3)C, Ac-GVK(me3)C, Ac-GLK(me3)C, Ac-ALK(me3)C, Ac-GFK(me3)C, Ac-GVGK(me3)C, Ac-GLGK(me3)C, Ac-GAGGK(me3)C, Ac-GL(abu)K(me3)C, Ac-GFGK(me3)C, Ac-GRGK(me3)C, Ac-GPAGK(me3)C, Ac-AYGK(me3)C, Ac-GPFK(me3)C, Ac-GVVGK(me3)C, Ac-G(abu)FGK(me3)C, Ac-GVFGK(me3)C, Ac-GVYGK(me3)C, Ac-GARGGK(me3)C, Ac-GAVV(abu)K(me3)C, Ac-GFYGK(me3)C, Ac-GYYGK(me3)C, Ac-GYYAK(me3)C, Ac-GPYFK(me3)C, Ac-GRGFGK(me3)C, Ac-GYFGGK(me3)C, Ac-GYYGGK(me3)C, Ac-AYYGGK(me3)C, and Ac-GYY(abu)GK(me3)C, wherein each Ac is an acetyl and each Abu is a 2-aminobutyric acid.

In various example embodiments, the set of molecules employed by the present invention can be selected from the libraries discussed below.

Table 1 describes example embodiments of chemical libraries suitable for practicing the present invention.

TABLE 1

| Library Name | Primary Physical Property | Underlying Principle |
|---|---|---|
| Fluorescence Capillary Electrophoresis (CE) | Emission Wavelength Electrophoretic Mobility | Charge, mass, hydrodynamic diameter, geometric anisotropy |
| Gas Chromatography (GC) | Volatility | Polarity, mass, partitioning coefficient |
| SAMDI Mass Spectrography | Mass | |
| Thin-layer chromatography (TLC) | Polarity | Molecular structure, local dipole moment |

In an example embodiment, peptides shown in Table 2, distinguishable by CE, can be used to practice the present invention:

TABLE 2

```
                                            (SEQ ID NO: 30)
Trp-Asp-Asp-Asp-Phe (SEQ ID NO: 31)
Trp-Asp-Asp-Asp-Leu (SEQ ID NO: 32)
Trp-Asp-Asp-Asp-Val (SEQ ID NO: 33)
Trp-Asp-Asp-Asp-Pro (SEQ ID NO: 34)
Trp-Asp-Asp-Asp-abu (SEQ ID NO: 35)
Trp-Asp-Asp-Asp-Ala (SEQ ID NO: 36)
Trp-Asp-Asp-Asp-Gly (SEQ ID NO: 37)
Trp-Asp-Asp-Asp (SEQ ID NO: 38)
Trp-Asp-Asp-Asn (SEQ ID NO: 39)
Trp-Asp-Asp-lys (SEQ ID NO: 40)
Trp-Asp-Asp-Asp-Asn (SEQ ID NO: 41)
Trp-Asp-Asp-Asp-lys (SEQ ID NO: 42)
Trp-Asp-Asp-Asp-Asp-Asn (SEQ ID NO: 43)
Trp-Asp-Asp-Asp-Asp-lys (SEQ ID NO: 44)
Trp-Asp-Asp-Asp-Asp-Asp-Asn (SEQ ID NO: 45)
Trp-Asp-Asp-Asp-Asp-Asp-lys (SEQ ID NO: 46)
Trp-Asp-Asp-Asp-Asp-Asp-Asp-Asn (SEQ ID NO: 47)
Trp-Asp-Asp-Asp-Asp-Asp-Asp-lys
```

TABLE 2-continued

```
                                            (SEQ ID NO: 48)
Trp-Asp-Asp-Asp-Asp-Asp-Asp-Asn (SEQ ID NO: 49)
Trp-Asp-Asp-Asp-Asp-Asp-Asp-lys (SEQ ID NO: 50)
Trp-Asp-Asp-Asp-Asp-Asp-Asp-Asp-Asn (SEQ ID NO: 51)
Trp-Asp-Asp-Asp-Asp-Asp-Asp-Asp-lys (SEQ ID NO: 52)
Trp-Asp-Asp-Asp-Asp-Asp-Asp-Asp-Asp-Asn (SEQ ID NO: 53)
Trp-Asp-Asp-Asp-Asp-Asp-Asp-Asp-Asp-lys
```

In another example embodiment, the following benzoate phenols, distinguishable by CE, can be used to practice the present invention.

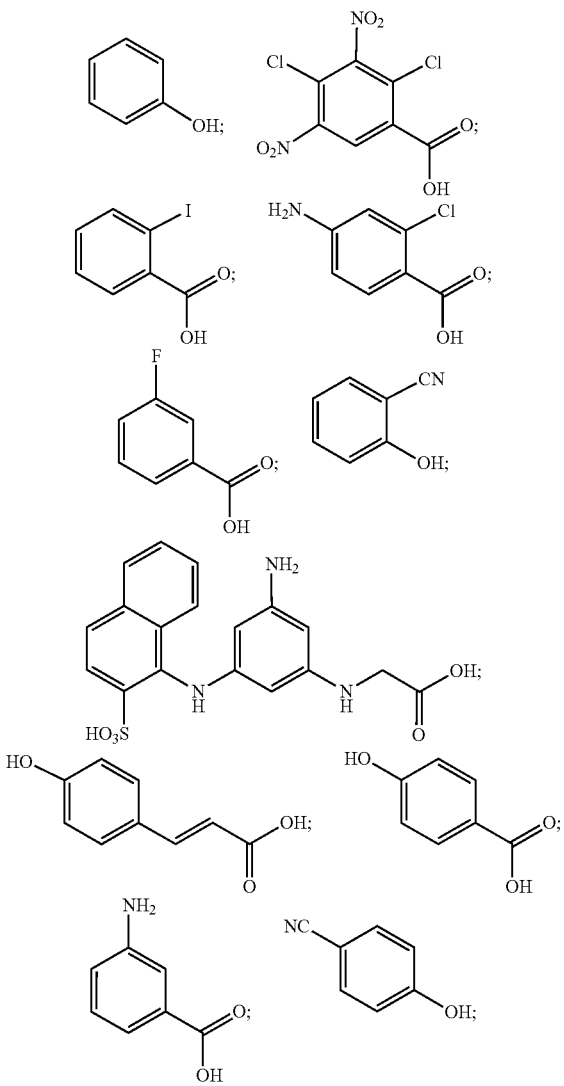

-continued
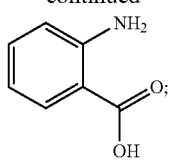
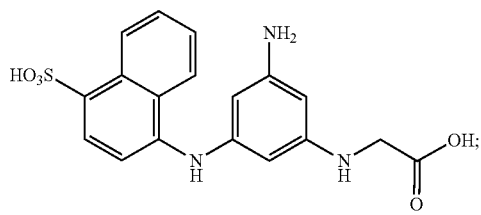
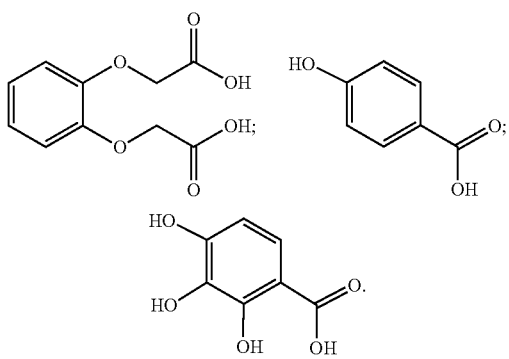
In another example embodiment, the following cyanurates, distinguishable by CE, can be used to practice the present invention:
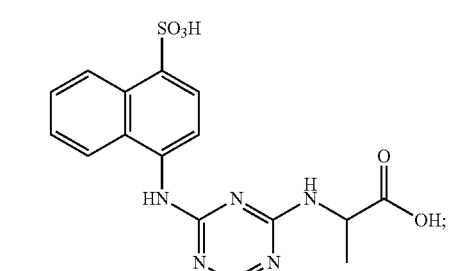
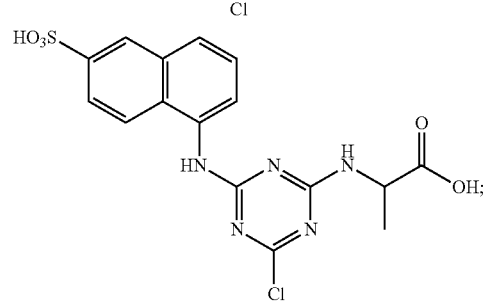
-continued
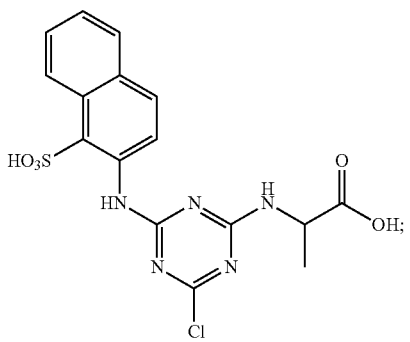
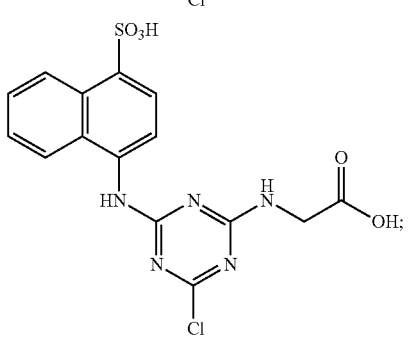
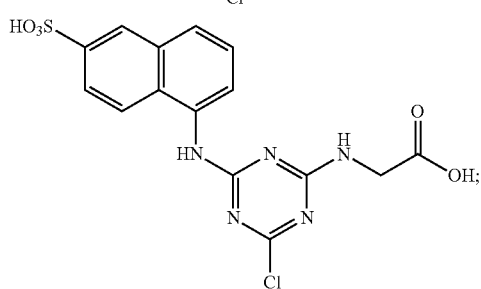
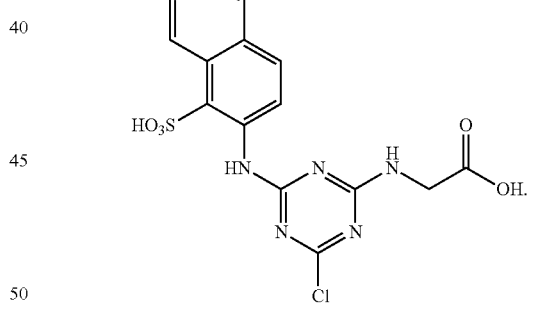
In another example embodiment, the following fluorescent dyes, distinguishable by fluorescent emission, can be used to practice the present invention:
Atto 425
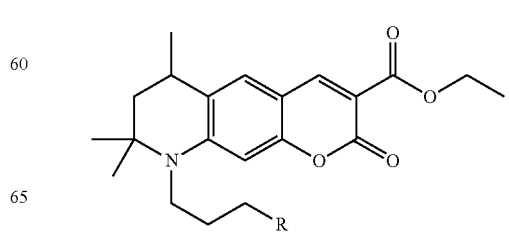

-continued
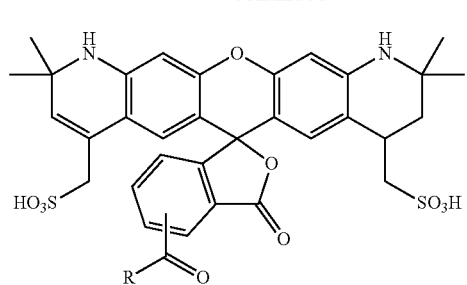
Alexa 568
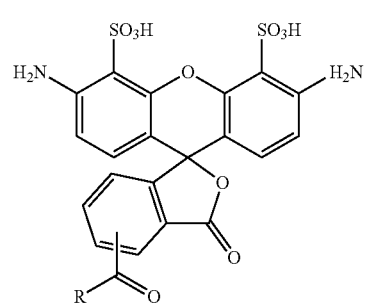
Alexa 488
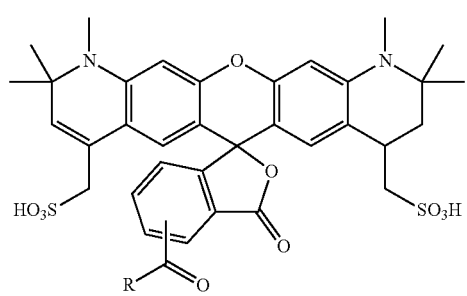
Alexa 594
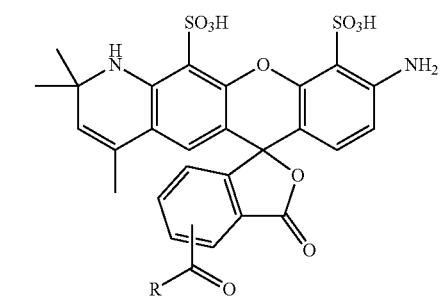
Alexa 514
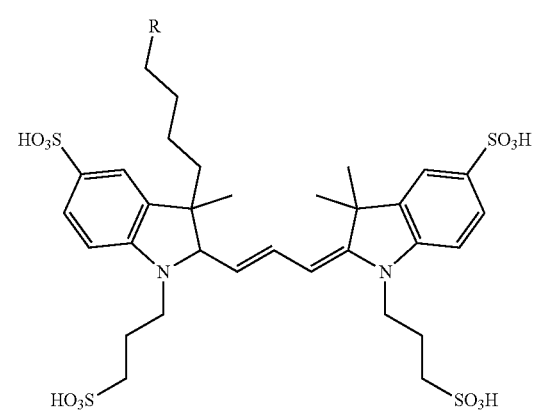
Alexa 647
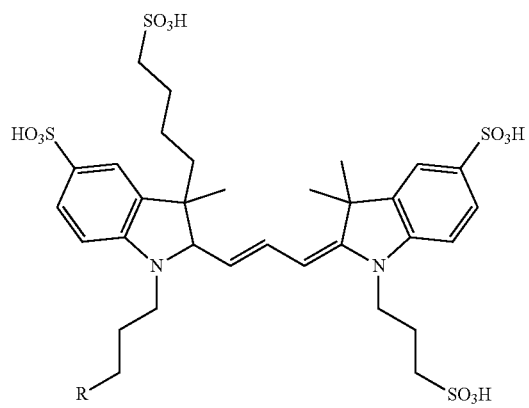
Alexa Fluor 555
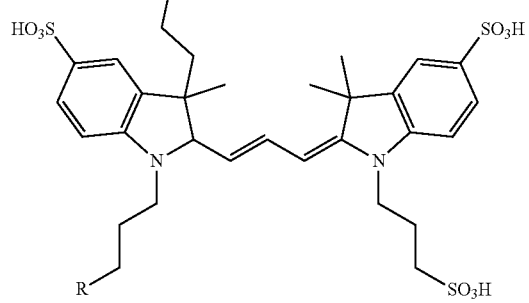
Atto 634
In another example embodiment, the following peptides, distinguishable by SAMDI Mass Spectrography, can be used to practice the present invention:
Leu   Val   Gly   Asn   Gly   Lys
Leu   Gly   Leu   Ser   Ser   Lys -continued

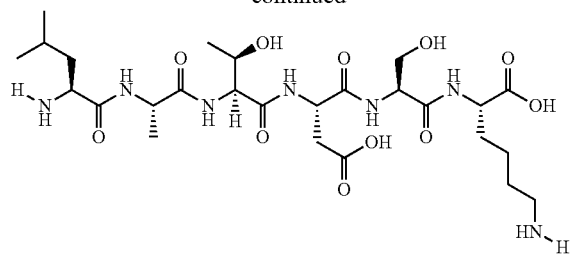

Leu Ala Thr Asp Ser Lys

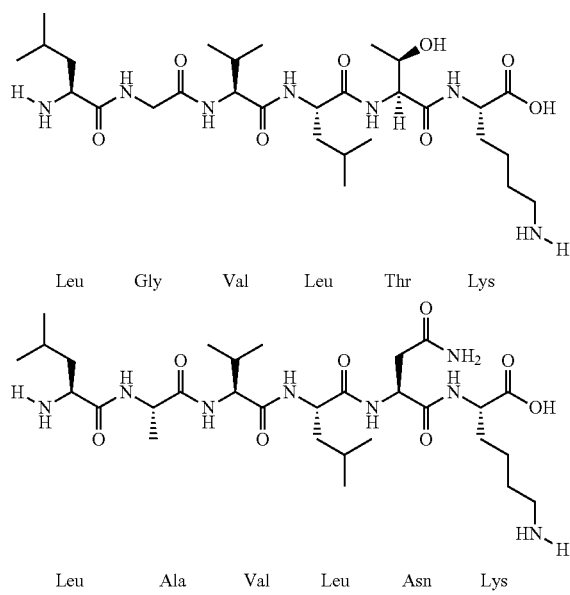

Leu Gly Val Leu Thr Lys

Leu Ala Val Leu Asn Lys

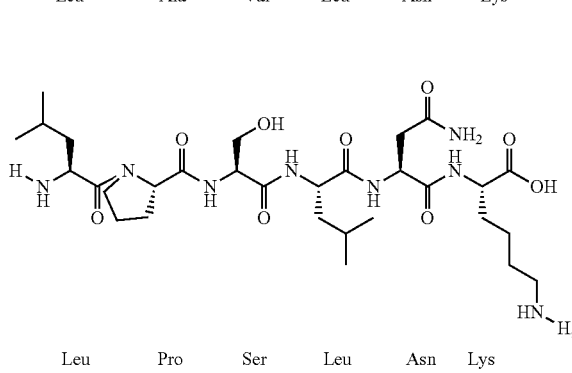

Leu Pro Ser Leu Asn Lys

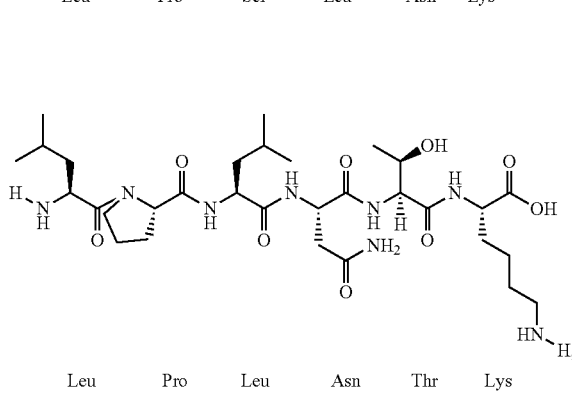

Leu Pro Leu Asn Thr Lys

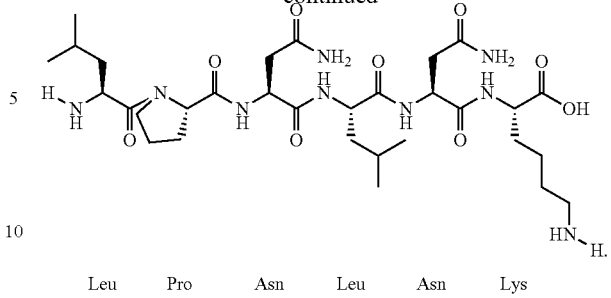

Leu Pro Asn Leu Asn Lys

In yet another example embodiment, molecules that can be employed in the practice of the present invention are molecules distinguishable by GC. Example library of such molecules are the products of the following reaction scheme:

(Scheme 1)

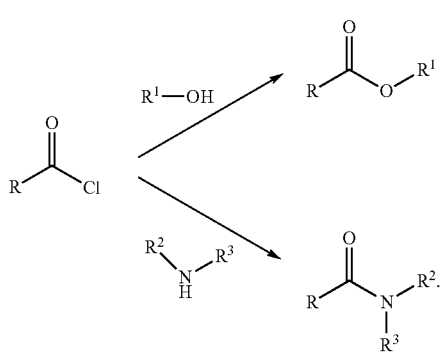

In Scheme 1, R is a $C_1$-$C_{24}$ alkyl, $R^1$ is a $C_1$-$C_8$ alkyl, $R^2$ and $R^3$, each independently, is a $C_1$-$C_6$ alkyl, or $R^2$ and $R^3$, together with the nitrogen atom to which they are attached, form a 4-7-member heterocyclyl that includes 1, 2 or 3 additional heteroatoms selected from N, O, or S.

"Alkyl" means an optionally substituted saturated aliphatic branched or straight-chain monovalent hydrocarbon radical having the specified number of carbon atoms. Thus, for example, "($C_1$-$C_6$) alkyl" means a radical having from 1-6 carbon atoms in a linear or branched arrangement. "($C_1$-$C_6$)alkyl" includes methyl, ethyl, propyl, butyl, pentyl and hexyl. "($C_1$-$C_{12}$) alkyl" means a radical having from 1-12 carbon atoms in a linear or branched arrangement. "($C_1$-$C_{12}$)alkyl" includes methyl, ethyl, propyl, butyl, pentyl, hexyl, heptyl, octyl, nonyl, decyl, undecyl and dodecyl. Unless otherwise specified, suitable substitutions for a "substituted alkyl" include halogen, —OH, —O—$C_1$-$C_4$ alkyl, $C_1$-$C_4$ alkyl, halo-substituted-$C_1$-$C_4$ alkyl, —O—$C_1$-$C_4$ haloalkyl, —NH$_2$, —NH($C_1$-$C_4$ alkyl), —N($C_1$-$C_4$ alkyl)$_2$, $C_3$-$C_{12}$ carbocyclyl (e.g., cyclopropyl, cyclobutyl, cyclopentyl, cyclohexyl, phenyl or naphthalenyl), a (4-13 membered) heterocyclyl (e.g., pyrrolidine, piperidine, piperazine, tetrahydrofuran, tetrahydropyran or morpholine) or —N($R^X$)($R^{X'}$), wherein $R^X$ and $R^{X'}$ are independently hydrogen or $C_1$-$C_4$ alkyl, or taken together with the nitrogen atom to which they are bound form a (4-7 membered) heterocylic ring optionally comprising one additional heteroatom selected from N, S and O, wherein the (4-7 membered)

heterocylic ring is optionally substituted with halo, —OH, halo-substituted $C_1$-$C_4$ alkyl, —$C_1$-$C_4$ alkyl, or —$C_0$-$C_4$ alkylene-O—$C_1$-$C_4$ alkyl.

The term "halo" means Br, I, Cl, or F.

"Alkylene" or "alkylenyl" (used interchangeably) mean an optionally substituted saturated aliphatic branched or straight-chain divalent hydrocarbon radical having the specified number of carbon atoms. An alkyl moiety of an alkylene group can be a part of a larger moiety such as alkoxy, alkylammonium, and the like. Thus, "($C_1$-$C_6$)alkylene" means a divalent saturated aliphatic radical having from 1-6 carbon atoms in a linear arrangement, e.g., —[($CH_2$)$_n$]—, where n is an integer from 1 to 6, "($C_1$-$C_6$) alkylene" includes methylene, ethylene, propylene, butylene, pentylene and hexylene. Alternatively, "($C_1$-$C_6$)alkylene" means a divalent saturated radical having from 1-6 carbon atoms in a branched arrangement, for example: —[$CH_2CH_2CH_2CH_2CH(CH_3)$]—, —[($CH_2CH_2CH_2CH_2C(CH_3)_2$)]—, —[($CH_2C(CH_3)_2CH(CH_3)$)]—, and the like. A "($C_1$-$C_{12}$)alkylene" includes methyl, ethyl, n-propyl, isopropyl, n-butyl, sec-butyl, tert-butyl, pentyl, hexyl, heptyl or octyl. A specific branched $C_3$-alkylene is

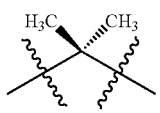

and a specific $C_4$-alkylene is

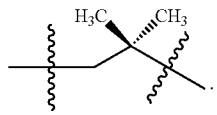

Other examples of a divalent $C_{1-6}$ alkyl group include, for example, a methylene group, an ethylene group, an ethylidene group, an n-propylene group, an isopropylene group, an isobutylene group, an s-butylene group, an n-butylene group, and a t-butylene group.

A "$C_0$ alkylenyl" is a covalent bond.

"Carbocyclyl" means a cyclic group having a specified number of atoms, wherein all ring atoms in the ring bound to the rest of the compound (also known as the "first ring") are carbon atoms. Examples of "carbocyclyl" includes 3-18 (for example 3, 4, 5, 6, 7, 8, 9, 10, 11, 12, 12, 1, 14, 15, 16, 17, or 17 or any range therein, such as 3-12 or 3-10) membered saturated or unsaturated aliphatic cyclic hydrocarbon rings, or 6-18 membered aryl rings. A carbocyclyl moiety can be monocyclic, fused bicyclic, bridged bicyclic, spiro bicyclic, or polycyclic.

"Hetero" refers to the replacement of at least one carbon atom member in a ring system with at least one heteroatom selected from N, S, and O. "Hetero" also refers to the replacement of at least one carbon atom member in an acyclic system. When one heteroatom is S, it can be optionally mono- or di-oxygenated (i.e. —S(O)— or —S(O)$_2$—). A hetero ring system or a hetero acyclic system may have 1, 2, 3 or 4 carbon atom members replaced by a heteroatom.

"Heterocyclyl" means a cyclic 3-18 membered, for example 3-13-membered, 3-15, 5-18, 5-12, 3-12, 5-6 or 5-7-membered saturated or unsaturated aliphatic or aromatic ring system containing 1, 2, 3, 4 or 5 heteroatoms independently selected from N, O and S. When one heteroatom is S, it can be optionally mono- or di-oxygenated (i.e. —S(O)— or —S(O)$_2$—). The heterocyclyl can be monocyclic, fused bicyclic, bridged bicyclic, spiro bicyclic or polycyclic. Non-limiting examples include (4-7 membered) monocyclic, (6-13 membered) fused bicyclic, (6-13 membered) bridged bicyclic, or (6-13 membered) spiro bicyclic.

"Aryl" or "aromatic" means an aromatic 6-18 membered monocyclic or polycyclic (e.g. bicyclic or tricyclic) carbocyclic ring system. In one embodiment, "aryl" is a 6-18 membered monocylic or bicyclic system. Aryl systems include, but not limited to, phenyl, naphthalenyl, fluorenyl, indenyl, azulenyl, and anthracenyl.

With respect to the compounds employed in Scheme (1), the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

Example compounds of general structural formula R—COOH that can be employed in Scheme 1 are those represented by the following structural formulas:

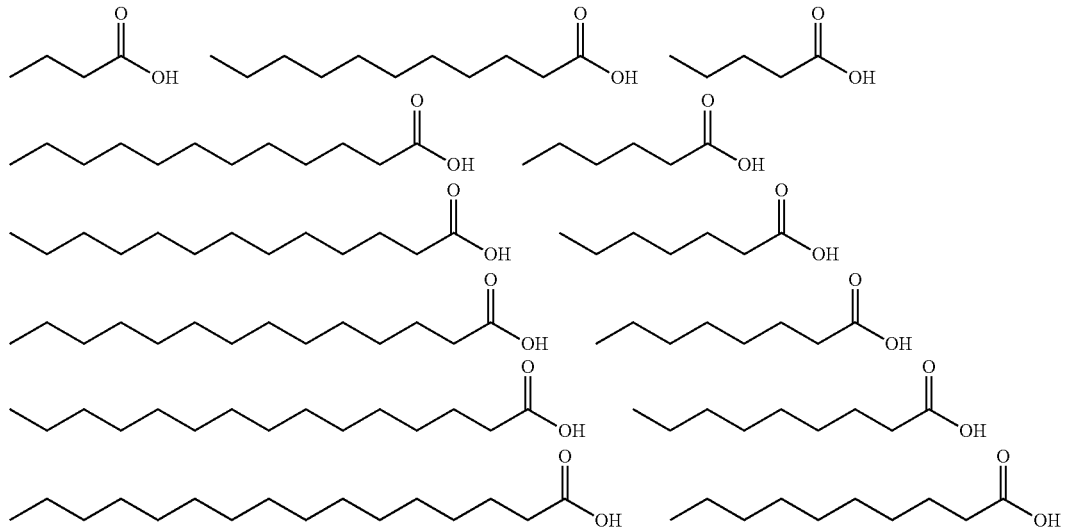

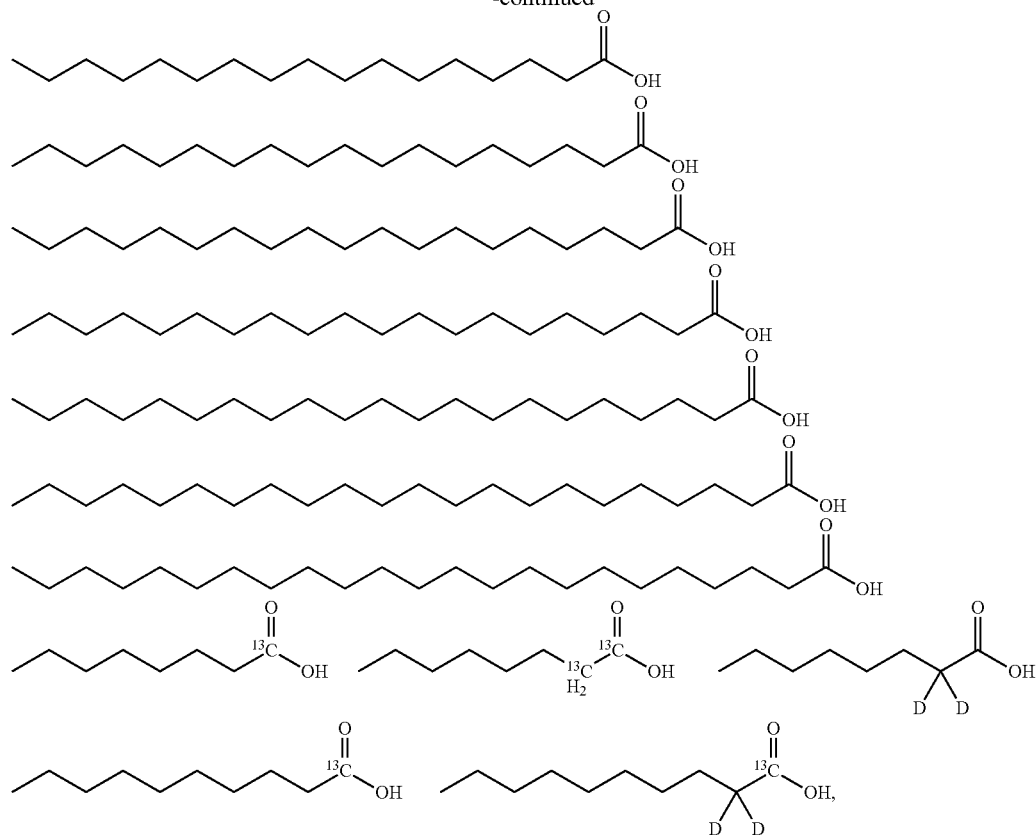
or acceptable salts thereof.
Example compounds of general structural formula $R^1$—OH that can be employed in Scheme 1 are those represented by the following structural formulas:
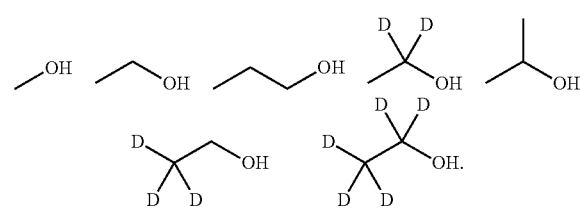
Example compounds of general structural formula $HNR^2R^3$ that can be employed in Scheme 1 are those represented by the following structural formulas:
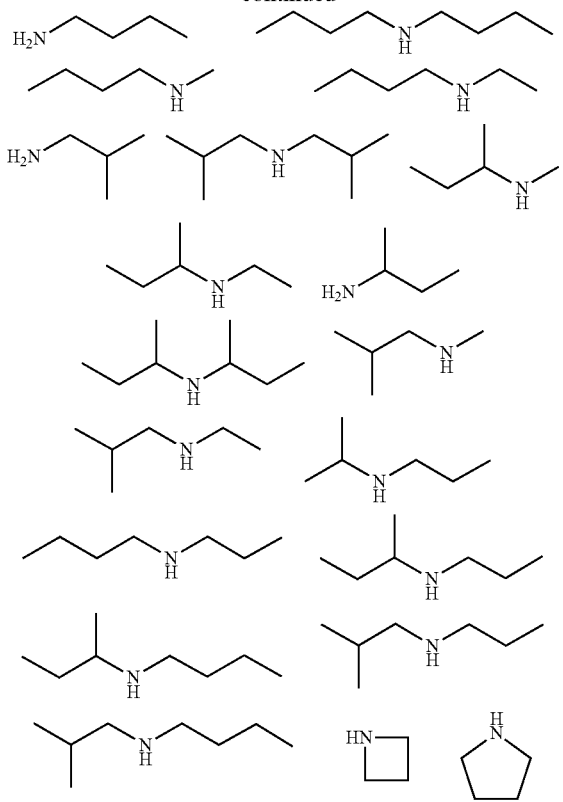

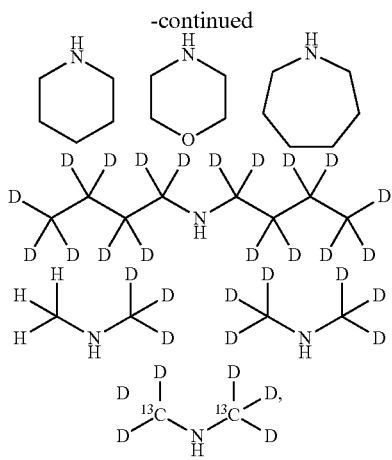

or acceptable salts thereof.

In exemplary embodiment, digital information is stored in mixtures of fluorescent Quantum Dots. Quantum dots have very sharp emission bands which help to resolve the presence or absence of the quantum dot within the mixture. A multichannel fluorescence detector in a fluorescent confocal microscope is able to, simultaneously and independently, resolve the presence or absence of each of the respective quantum dots in the mixtures at a given location on a substrate. In the below example, the quantum dots are printed onto a polymer substrate using ink-jet printing, and optical read-out provides a parallelized read-out of the stored digital information. However, it will be appreciated that a variety of additional methods may be used to deposit readable quantum dots on a substrate.

As discussed above, in order to preserve information over long timescales, reduce energy consumption and resist tampering, new approaches and materials are required for its storage. Alternative devices including optical and magnetic media such as hard disks and flash memory have insufficient operational lifetimes for long-term storage (typically less than two decades) and/or require energy to maintain information. Inorganic crystals (e.g., quantum dots) can be used to store information without power, at high density, and can be stable for thousands of years or more.

Quantum dots (QDs) are semiconductor particles a few nanometres in size, having specialized optical and electronic properties. When quantum dots are illuminated by UV light, an electron in the quantum dot can be excited to a state of higher energy. In the case of a semiconducting quantum dot, this process corresponds to the transition of an electron from the valence band to the conductance band. The excited electron can drop back into the valence band releasing its energy by the emission of light. The color of this light emission (photoluminescence) depends on the energy difference between the conductance band and the valence band. Their optoelectronic properties change as a function of both size and shape. For example, exemplary quantum dots of 5-6 nm diameter emit longer wavelengths, with colors such as orange or red. Smaller exemplary quantum dots of 2-3 nm emit shorter wavelengths, yielding colors like blue and green. However, the specific colors vary depending on the exact composition of the quantum dots. It will be appreciated that a variety of quantum dots are known in the art. Examples of Quantum Dots suitable for practicing the present invention include:

1. Core/shell quantum dots, where the examples of the core include Cadmium Selenide, Cadmium Sulfide, Indium Phosphide, Indium Arsenide, Copper Indium sulfide, Zinc Selenide, Silver Sulfide. A Shell of these quantum dots can include Zinc sulfide, Zinc selenide, Cadmium sulfide, or any combination of these above materials (called alloyed quantum dots)

2. Single element fluorescent materials, for example: Carbon quantum dots, Graphene quantum dots, Silicon quantum dots.

3. Perovskite quantum dots, for example: Cesium lead halides, methyl ammonium lead halides, etc. These materials could also be passivated (made more stable to ambient conditions) using organic/inorganic ligands and other surface chemistries.

4. Layered materials like MoS2, MoSe2, WS2, etc.

5. Epitaxially grown quantum materials like GaAs, InGaAs, etc.

The term "quantum dot" is not limited to a quasi-0 dimensional geometry. The geometry of these fluorescent particles can be nanorods (1-dimensional), nano-platelets (2-dimensional), etc.

EXEMPLIFICATION

Example 1: The Use of a Collection of Oligopeptides to Store Information

Materials and Methods

Preparation of solutions of oligopeptides (molbits): Oligopeptides were synthesized using standard Fmoc chemistry on rink-amide resin and purified by HPLC. Stock solutions of each oligopeptide were made in 0.1% TFA with DI water and stored at −20° C. To prepare the oligopeptides and oligopeptide mixtures for immobilization, each oligopeptide stock solution was distributed into a source plate. Mixing of oligopeptides to form binary data sets was performed using these oligopeptide stock solutions and a Echo® 555 (Labcyte Inc.) liquid handler, with the final concentration of each oligopeptide, when present, at 20 µM (some sequences had to be diluted further to maintain comparable ionization to the other analytes). A Python program written in-house was used to assign oligopeptides from alphanumeric character inputs (translated to ASCII) and bitstrings.

Generating input tables for automated encoding of text: To generate an input table for alphanumeric text for the Echo® 555 liquid handler, a given text was first divided into sections of 6,144 characters (the maximum number of characters that fit on SAMDI 1,536-spot target plate). These blocks of text were then run through a program that further divided the 6,144 characters of each block into four sections of 1,536 characters. Each section of 1,536 characters was then assigned to a 384 well plate, with 4 characters (bytes) per well, and a text file (extension .txt) was generated containing the string of characters for each well plate. This file was then used in the program titled "Molbit Encoding". The program also required inputs for the volume for each stock solution of oligopeptide to be transferred (in nL), the total capacity per source well (the location of a given oligopeptide to be transferred), the name of the destination plate, and a list of the ASCII binary combinations for each of the characters used. Once it received the required inputs, the program matched each character in the .txt file to the appropriate binary ASCII combination and generates an input table for the Echo instrument, including information on source well, transfer volume, destination well, and destination plate name.

Generating input tables for automated encoding of an arbitrary bitstream: To generate an input table for non-ASCII data for the Echo® 555 liquid handler, a bitstream was first generated. The bits were then sequentially numbered 1 through 32. After this process the "Vlookup" function in excel was used to assign a predefined source well for each number. Each group of 32 bits was next assigned with a well of a 1,536-well destination plate. The bitstream, with each entry's associated bit number, source well, and destination well, was then reduced to include only those entries with a bitstream value of 1. Next the "Vlookup" function was used to assign the transfer volume for each entry, based on the source well. Finally, these entries were transferred into an Echo input table, with information on source well, transfer volume, destination well and destination plate name.

Automated encoding via liquid transfer: Prior to initializing a run on the Echo® 555 liquid handler robot, a source plate (Labcyte Echo Qualified 384-well plates, Cat #: PP-0200) was prepared with the desired oligopeptides to be transferred. Each well of the source plate contained 65 μL of each of the 32 stock solutions (2 mM in oligopeptide). The number of wells needed for each oligopeptide was determined from the input table generated via the encoding program. The source plate and destination plate (Greiner Bio-One 384-well plates Cat #: 784201) were placed in storage towers in the Access Laboratory Workstation attached to the liquid handler. To initiate the run, the input table was imported, which defines the locations of the source and destination plates, and the protocol was executed. Once the oligopeptides were transferred, the destination and source plates were covered with lids (Labcyte MicroClime Environmental Microplate Lid Cat #: LL-0310) to ensure that the contents of the plates did not dry.

Preparation of monolayer arrays: Array plates with 384 and 1536 gold spots on steel plates were soaked in a solution of a mixture of EG3-capped alkane disulfide and a mixed disulfide of EG3-capped alkanethiol and a maleimide-terminated EG3-capped alkanethiol for 24 hours, at room temperature, to allow formation of a self-assembled monolayer on the gold surface. The solution of disulfides contained an overall concentration of 1 mM of the two monolayer compounds in a stoichiometric ratio (2 to 3) to yield a monolayer wherein the maleimide groups were present at a density of 20%. Following monolayer formation, the plates were soaked in a solution of hexadecyl phosphonic acid (10 mM) for 5 minutes, and rinsed with ethanol, water, ethanol, dried with nitrogen and stored dry under vacuum. SAMDI plates were used within one week of forming monolayers.

Immobilization of peptides onto plates: Prior to immobilization, the peptide mixture plates generated by the Echo® 555 liquid handler were filled with 4 μL of 100 mM Tris buffer at pH 8.0, with a ThermoFisher Multidrop Combi, to ensure the solutions of mixed oligopeptides were at the correct pH and appropriate concentration for conjugation to the monolayer. Each set of four 384-multiwell plates were then transferred to a 1,536-spot SAMDI plate functionalized with 20% maleimide and displaying a hexadecyl phosphonic acid background between spots. Samples (0.75 μL) from each well of the 384-multiwell plate that contained solution were transferred onto the 1,536-spot SAMDI plate utilizing the TECAN Fluent/Freedom Evo instruments, with a MCA 384 head utilizing 15 μL tips, such that each 384-multiwell plate was transferred to one quadrant of a 1536-spot SAMDI plate. In this way the spots were read left to right and top to bottom, and allowed the original encoded text to be read. Once transferred, the peptide solutions reacted with the maleimide groups on the surface of the plate for 10-30 minutes, in a humidified chamber, to covalently immobilize the mixture of peptides. After immobilization, the plate was washed with ethanol, water, ethanol and dried under a stream of nitrogen.

MALDI-TOF MS analysis: SAMDI plates with immobilized oligopeptides were first treated with 2',4',6'-trihydroxyacetophenone matrix solution (THAP, 12 mg/ml in acetone) and then were loaded into an ABSciex TOF-TOF 5800 instrument. Matrix-assisted laser desorption/ionization time-of-flight mass spectra were collected for each spot in positive mode with the instrument setting of 700 shots/spectrum, 5300 laser intensity, stage velocity of 1500 μm/s, 0.61 digitizer setting, and a laser pulse rate of 400 Hz.

Analysis of spectra with program: Prior to analysis of the SAMDI spectra, an input table was generated containing the peptide mass combinations for each of the 95 printable ASCII characters used for each of the 4 bytes. This input table was then divided so that each contained only the peptide combinations for the corresponding byte. This division was done using the "Molbit Decoding" program along with an input of the 95 ASCII characters in quadruplicate, once per byte, and a list of the peptides for each character and byte.

The SAMDI spectra were exported from the instrument computer and analyzed using the "new profiler" program. This program required the following inputs to run; location of the mass spectrum files, location for the output of generated files, an input table for the byte (1-4) being analyzed, as well as the background threshold. The background threshold was a user-determined value; it was based on the absolute peak intensity relative to the highest peak in the spectrum and was usually set between 20-30%. The background threshold helped avoid false positives in detecting presence of molbits due to the noise in the spectra.

The program functioned in the following way. It first scanned the spectrum and identifies the maximum intensity value (arbitrary units) and set this value to 1. It then converted each of the other intensities to relative intensity units based on this parent value. The software then removed any value below the threshold set by the user and generated a new list containing only those peaks remaining above the threshold. Following the generation of the new list, it summed the values of the intensities by rounding to the nearest integer mass value. It then attempted to generate groups of masses based on the two highest consecutive intensity units, followed by single mass intensity groups that could not be combined. At this point, the program scanned the input table to find an entry that provides the highest sum of intensities based on mass groups present. Once it found the entry, it returned the value for the character for which it had decoded. If it failed to match an entry in the input table it returned a "FAILED" response and moved on to the next spectrum. Once the software finished running through the entire dataset, it produced a file that listed the label of the data spot, the decoded character (if applicable), as well as the masses that had been identified for that character. Recovery of information was determined by the number of correctly identified molbits by spectral analysis, divided by the total number of molbits originally encoded, multiplied by 100.

Image compression, encoding, storage, retrieval, and reconstitution: First, if the original copy of an image was larger than the storage space available on one SAMDI 1,536-spot plate (6,144 bytes), that image was compressed, via the JPEG algorithm, to fit on one well plate. The JPEG algorithm was implemented with Adobe Photoshop CS4, version 11.0, with the JPEG quality and blur settings indicated in Supplementary Information Table 2 using the "Save for Web and Devices" function.

After compression, the JPEG files were encoded as bitstreams using the program titled "Image Encoding" (see Supplementary Information for source code), run in Matlab R2015b. The code read the bytes stored on the local computer hard drive that comprised the JPEG file, and converted these bits to a bitstream. The length of the data contained in the bitstream, in bits, was also read by the code and prepended (as a 16-bit segment) to the front of the bitstream, which was then encoded onto the well plate using the automatic molecular encoding process described above.

Retrieval of data from the well plate was performed as described above, where the output from reading the SAMDI plate was a bitstream. This bitstream, in the form of a text (.txt) file of "1" and "0" with no other characters, was read by a program titled "Image Extraction", which extracted the length of the image file from the first 16 bits of the bitstream and then retrieved that quantity of bits from the bitstream, starting at the 17th bit (after the string of bits that recorded the length of the file). This image data was reconstituted into an image file in JPEG format which can be interpreted and displayed by a computer. The error rate during retrieval and reconstitution of each image was computed.

Results and Discussion

The objective of the present study was to explore the uses low molecular weight molecules to store information. Macromolecules that require organic synthetic steps to manufacture, and which usually each encodes a separate message per molecule was specifically avoided. Instead, sets of oligopeptides having distinguishable molecular weights were used to store information. Overall, the tested system requires a set of a maximum of eight oligopeptides, as a mixture, in a microwell, to store one byte, and a mixture of 32 oligopeptides to store four bytes. These systems are also capable of writing any arbitrary binary information using the same set of small molecules. Reading is accomplished by identifying the masses of the molecules that are immobilized to a self-assembled monolayer (primarily as disulfides from the laser desorption process) using mass spectrometry (MS). MS provides both high precision (enabling accurate determination of the composition of mixtures of oligopeptides in a single sub-millimeter spot of an immobilized array, without separation, and with few errors) and high rates of reading.

The initial demonstration has been to write messages in eight-bit ASCII code, convert them to an equivalent molecular code, store them on an array plate (four bytes per spot), and read them using SAMDI (self-assembled monolayers for matrix-assisted laser desorption/ionization) mass spectrometry. ASCII (American Standard Code for Information Interchange) is a look-up table that includes the alphabet, numbers, punctuation, and special characters—a maximum of 256 characters—and is used primarily for alphanumeric text.

FIG. 1 presents Table 1 that summarizes this strategy for the letter "K."

FIG. 2 presents Extended Data Table 1 that summarizes a complete assignment of oligopeptides sufficient to encode four bytes in a single mixture, with their assignments to a binary molecular representation.

To differentiate electronic storage and its theoretic foundation in Boolean algebra, and molecular storage, the equivalent of a bit, and of an eight-bit byte, of information—in the form of mixtures of molecules—are referred to as a "molbit" and a "molbyte." To store information in molecules, a method was designed that allowed to encode ASCII in molecules distinguishable by mass spectrometry. For example, the letter "K" in ASCII is represented by one byte (01001011) in binary. This binary representation was converted to a molecular one by assigning an oligopeptide to each of the eight bits in a byte, and include that oligopeptide on the spot if the bit value is "1" and omit it if the bit value is "0" (FIG. 1, Table 1).

These oligopeptides were selected to have four characteristics: i) All were resolvable by mass using SAMDI as components of a common mixture (FIG. 1). The different amino acids in each oligopeptide were covalently bonded, but their order was not relevant—only the total mass. The oligopeptides were not covalently bonded to one another, and did not form macromolecules. Information was thus stored as mixtures of low molecular weight (MW<1,000 g mol-1) molecules, in arrays, specifying "1" and "0" in a binary representation, rather than as a sequence of groups in a linear polymer. ii) All oligopeptides terminated in a cysteine to allow efficient immobilization by Michael addition to the reactive maleimide group present in the 1.25-mm diameter spot of the SAMDI plate. iii) Each oligopeptide included a trimethyllysine ($K^{Me3}$) with a fixed positive charge to aid in mass spectrometry (positive mode). By using the set of 32 peptides listed in FIG. 2, Extended Data Table 1, each of which is distinguishable in a mixture containing the others, the information could be stored for four molbytes (e.g., four letters in ASCII) in one spot.

Using this method, the presence of a particular peptide in a mixture indicated three parameters: i) The byte to which it is contributing information; ii) its location in the bitstring of that byte; and iii) its value ("1"). The absence of that peptide indicates that that position in the molbyte is "0". The presence of the four oligopeptides listed in FIG. 1, Table 1 were thus assigned to bits with the value 1, and the four oligopeptides absent from the mixture were assigned to bits with the value 0. The one remaining parameter to be defined was the position of this letter in the sequence in the text: this information was provided by the position of the spot in the sequence of spots on the SAMDI array plate. The attractive feature of this method was that only eight oligopeptides allowed the specification of all of the characters of one byte, and thus allowed an arbitrary message to be written in ASCII (or any character set of 256 members); by using 32 distinguishable oligopeptides four bytes in one spot could be specified.

The schematics of the tested design is illustrated in FIG. 3. FIG. 3(A) is an illustration of oligopeptide molbits containing an information region that consists of one to five amino acids (chosen from 2-aminobutyric acid, alanine, arginine, glycine, leucine, phenylalanine, proline, tyrosine, valine), which provides a distinguishable mass-to-charge ratio for each peptide (a difference of 6-42 a.m.u.), a charge residue (trimethyl lysine), and an anchor residue (terminal cysteine). The N-terminus was capped by an acetyl group for chemical stability. FIG. 3(B) represents a schematic diagram showing an example of two immobilized oligopeptides (corresponding to molbit 1 and molbit 2 in panel (C) of FIG. 3) to a maleimide-terminated monolayer for storage. Prior to conjugation of oligopeptide(s), the monolayer consisted of a mixture of triethyleneglycol undecanethiol ($EG_3$-capped alkanethiol) terminating in either an alcohol or maleimide. FIG. 3(C) is a spectrum of a SAMDI spot containing all 32 molbits; the intensity was normalized to the highest signal. Oligopeptides were grouped by molecular weight into sets of eight, representing a byte of information (4 bytes total). The single-letter codes of residues in the information region are listed above each peak in the mass spectrum (see FIG. 2, Extended Data Table 1 for full list of peptide sequence and corresponding masses). The observed masses were for mixed disulfides derived from a $EG_3$-capped alkanethiol and the oligopeptide conjugated to a maleimide-terminated $EG_3$-capped alkanethiol.

FIG. 4 outlines the process that was used to 'write', 'store' and 'read' text using this set of 32 peptides. For a particular byte, the appropriate set of oligopeptides representing "1"s in the bitstring was deposited and mixed in wells of a 384 well plate using an Echo® 555 liquid handler. A Tecan® liquid handler than transferred these mixtures to an array plate having 1,536 gold islands ("spots"), each presenting a self-assembled monolayer. The peptides reacted covalently with the terminal maleimide groups present on the monolayers of the array plate. Covalent coupling prevented the components of the mixture from spreading on the surface and allowed their analysis with SAMDI mass spectrometry. The plate, with the completed text encoded as mixtures of oligopeptides in spots ordered on the plate, was stored. Reading by SAMDI was accomplished as described previously.

In particular, and referring to FIG. 4, "writing" was performed by first translating information (here, the alphanumeric characters of Feynman's lecture "There is plenty of room at the bottom") into binary. Binary information was converted to oligopeptides immobilized on a self-assembled monolayer, for storage. A MALDI-TOF mass spectrometer analyzed ("read") these plates. A program decoded the information in the spectra and generated a bitstring that was used to regenerate the original text. Recovery of information was determined by (number of correctly identified molbits)/(total number of molbits)×100.

This strategy for writing and reading bytes allowed a small number of low molecular weight molecules to encode many forms of information and, once synthesized, avoided the need for further synthesis to store a new message. (In this demonstration, to order these molbytes, an array plate was used in the format of a conventional microwell plate.) The density of information (D) that could be put on a plate depended on the representation, but here was given by $D=(molbytes/cm^2)=(wells/cm^2)/plate)(molebyte/well)$. For the tested system, this number was $D=64$ bytes/cm$^2$.

The system described herein was used to store both text and JPEG images. The procedure was operationally simple. The small number of molecules required (within a given set such as oligopeptides) needed only be synthesized once, and served to encode a very wide range of information. The text of Feynman's famous lecture "There is plenty of room at the bottom," was used as a demonstration of current capability. It was written, stored, and read with 99.9% recovery of information. This text (38,313 bytes or alphanumeric characters) was written and read using one set of devices (see FIG. 4) in 20 hours. The speed of 'writing' was 8 bits/s, and 'reading' was 20 bits/s, without parallelization. This process was amenable to simple linear parallelization, particularly since each line of instruments could be writing different information at the same time, using a shared set of molecules for storage: the speed could thus easily be increased by a factor of ten or more, albeit at ten times the capital cost. Higher density of spots in arrays and faster liquid transfer (which could be achieved by inkjet printing) can also increase the density and rate of writing information.

The example described herein employed oligopeptides, but many other classes of organic molecules (additional unnatural amino acids, fatty acids, aromatics including heterocycles, saturated terpenes, and others) can also be used: the described method thus has broad scope.

Oligopeptides have stabilities of hundreds or thousands of years under suitable conditions; i.e., in the absence of light (or ionizing radiation), oxygen or other oxidants, and high temperatures, and possibly in the absence of water, in inert containers. Importantly, occasional breaks in individual molecules would (unlike breaks in DNA) not significantly damage the fidelity of reading, since they would appear at masses that are not coded by the molbits. Molecular storage of information should be especially resistant to hacking electrically, magnetically, or optically, since the only way to read or rewrite the composition of information stored molecularly would be to access the molecules physically, and then to perform chemical processes.

For the organizations in need of archiving vast amounts of data, the disclosed methods and devices for storing information in mixtures of molecules can enable a stable archive that persists almost indefinitely and consumes little or no energy. Unlike sequence-dependent polymer-based methods like DNA, the storage in mixtures of stable molecules provide the advantage that writing information does not involve time-consuming synthesis of long molecular chains, which leads to writing times that are 1000 times slower than the disclosed approach. Additionally, fast writing and reading times, and the inexpensive cost of materials, makes this approach ideal for barcoding and verification of products along the international supply chain, thus protecting companies, governments, and consumers from fraud, counterfeiting, and theft.

It will be appreciated that the present disclosure is not limited to the polymer-based examples provided herein. Mixtures of non-polymeric molecules, including small molecules, may be used to store and retrieve information using the media and methods described in the present disclosure.

Example 2: Storage of Information in Mixtures of Fluorescent Quantum Dots

The present disclosure provides digital information storage using mixtures of quantum dots while addressing the requirement for sufficient read/write speeds, retention of information, density of information, and cost. In the below example, an inkjet printer enables writing at a rate of 127 bits/sec, and a multichannel fluorescence detector in a confocal microscope allowed reading at a rate of 121 Bytes/sec. Using this approach, the below example demonstrates writing 14,075 Bytes of digital information on a 7.5 mm×7.5 mm surface with subsequent reading over 1,000 times without loss in fluorescent signal intensity. Using quantum dots and inkjet printing, high information density and fast read/write speeds are obtained while enabling multiple reads of the stored data.

Devices such as optical disks, flash drives, and hard disk drives have operational lifetimes on the order of decades. Thus, maintaining digital archives requires constant replication of information stored on these devices. An alternative approach to using CMOS-based devices is to store information in molecules. As described herein, molecular-based storage systems can have very high storage densities and half-lives that can extend millions of years.

In this example, the storage of information in optical characteristics of quantum dots is demonstrated. Specifically, fluorescence of quantum dots is used in an optical information storage system. Information is written by ink-jet printing dilute solutions of the quantum dots on a polymeric substrate. Reading of the information is carried out using a confocal microscope equipped with a multichannel detector that can resolve, simultaneously and independently, any combination of the fluorescent signatures of the dots on the substrate. This optical read-out takes advantage of parallelized reading and is fundamentally different from other optical storage methods.

Alternative optical storage media uses laser beams to record and retrieve digital (binary) data. A laser beam encodes data onto a substrate in pits and lands on the disk's surface. Write-once optical discs use an organic dye recording layer while rewritable discs use a phase change alloy material (for example, AgInSbTe—an alloy of silver, indium, antimony, and tellurium). In such media, only a binary 0 or 1 is recorded at a location. In contrast, the present examples use 8 organic fluorescent dyes to write information. The corresponding reading technique can simultaneously and independently distinguish the presence or absence of each dye molecule at a location, which enables recording any combination of 0, 1, 2, 3, 4, 5, 6 and 7 simultaneously at the same location.

In this example, the substrate is an epoxy polymer which contains reactive amino groups. The n-hydroxy succinimide (NHS) functionalized quantum dots react on the substrate to form stable amide bonds. These covalently immobilized dyes are stable to more than 1000 reads without loss of intensity. Photobleaching does not significantly affect the stored information.

There are several advantages of this technique as compared to alternative long term storage techniques. These advantages include: (1) storage persistence without power; (2) high information density; and (3) availability of chemical encryption systems. For example, as the printed patterns do not need to overlap, the patterns can be misaligned or printed in completely different locations. In this way, information can be obfuscated, and the order of reading the patterns provides the key for decrypting the information.

Results and Discussion.

Choice of dyes: Seven fluorescent core-shell Quantum dots (mixture of Cadmium selenide-cadmium sulfide and zinc selenide-zinc sulfide quantum dots) were chosen to demonstrate the strategy. This technique can be expanded to incorporate any number of quantum dots in a mixture. The dots are dissolved in a solvent (hexane) and inserted in the ink-jet printer cartridge.

Quantum dots may be made of binary compounds such as lead sulfide, lead selenide, cadmium selenide, cadmium sulfide, cadmium telluride, indium arsenide, and indium phosphide. Quantum dots may also be made from ternary compounds such as cadmium selenide sulfide.

Writing information: Material deposition techniques like ink-jet printing and aerosol-jet printing enable microfabrication with high-throughput. In this example, ink-jet printing was used to print 1 pL drops at 30 μm spot size on the substrate. To demonstrate high-density information storage, the first section of one of the seminal research papers in human scientific history was written—"Experimental researches in electricity" by Michael Faraday, Phil. Trans. R. Soc. Lond. 1832, 122, 125-162. This text contains 14075 characters (i.e. 14075 bytes).

Choice of Substrate: Long term storage requires formation of thermodynamically stable bonds that have very long half-lives. An amide bond is one of the most thermodynamically stable bonds available to organic chemists. In this strategy, quantum dots were used that carry n-hydroxy succinimide ligands that will spontaneously react with amino groups on the substrate to form amide bonds. A crosslinked epoxy polymer is synthesized where a slight excess of the amine curing agent was used, which imparts reactive amino groups in the substrate. The epoxy polymer is synthesized by hot-pressing a mixture of bisphenol-A-diglycidyl ether and triethylene tetramine at 90° C. on a cellulose acetate sheet. The pressure to obtain 10 μm thick films.

Figure 5:
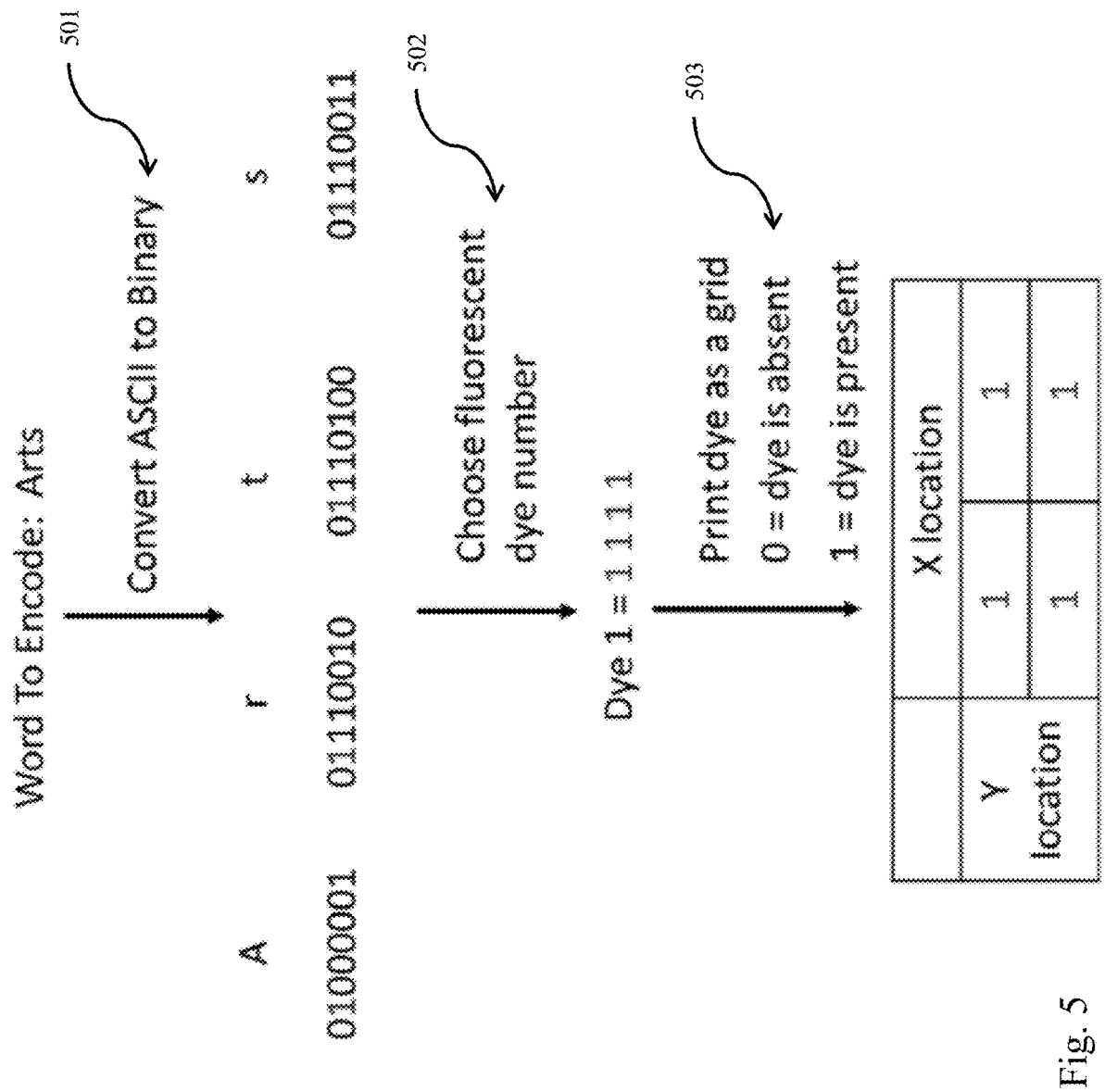
FIG. 5 is a flowchart illustrating a pattern generating scheme for writing of digital information using quantum dots according to embodiments of the present disclosure.

Pattern generating scheme: Referring now to FIG. 5, a flowchart is provided illustrating a pattern generating scheme for writing of digital information using quantum dots according to embodiments of the present disclosure. For example, if the word "Arts" needs to be written, the ASCII text is converted to binary digits at 501. Then, for DOT 2, the second position of each binary representation is selected at 502. The string of these binary digits are distributed in a grid at 503 (e.g., a 2×2 square for 4 letters). Using 0 as absence of the dye and 1 as presence of the dye, this information is written by printing this pattern onto the substrate. This process is repeated for all 8 positions of the binary representations. In total, 8 patterns are generated and printed at the same location onto the substrate.

These patterns need not be perfectly aligned, as the information present in the pattern of one DOT is independent of the information present in the pattern of another DOT. Thus, these patterns can even be printed in completely different locations (for example, these patterns can even be distributed at different physical locations) and the information can be decoded by the knowledge of just the order of stacking of the patterns).

Binary representation of ASCII characters contains 8 digits, but the first digit is always 0 for printable characters. Thus, the first DOT pattern is always a blank pattern.

Writing parameters: In this example, it took 116 sec on an average to write each of the 7 patterns for "Experimental researches in electricity" at 30 μm resolution on a 7.5 mm×7.5 mm substrate area.

Figure 6A:
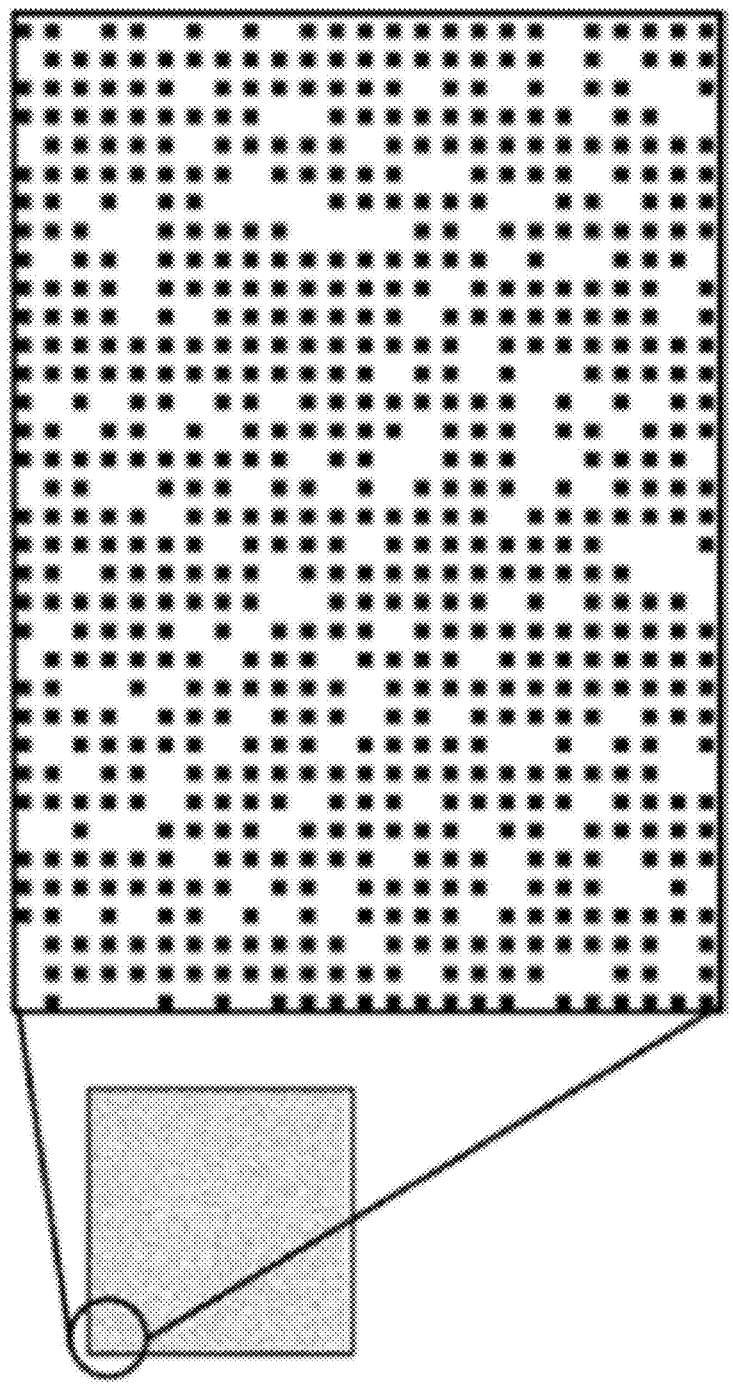
FIG. 6A is an image of an exemplary pattern generated by an encoding scheme according to embodiments of the present disclosure.

Referring to FIG. 6A, an exemplary pattern generated by the encoding scheme described above is illustrated. Each black square signifies the presence of a given quantum dot material on the substrate. Although in this example, the encoding material is deposited on a grid pattern, it will be appreciated that alternative patterns may be used.

Figure 6B:
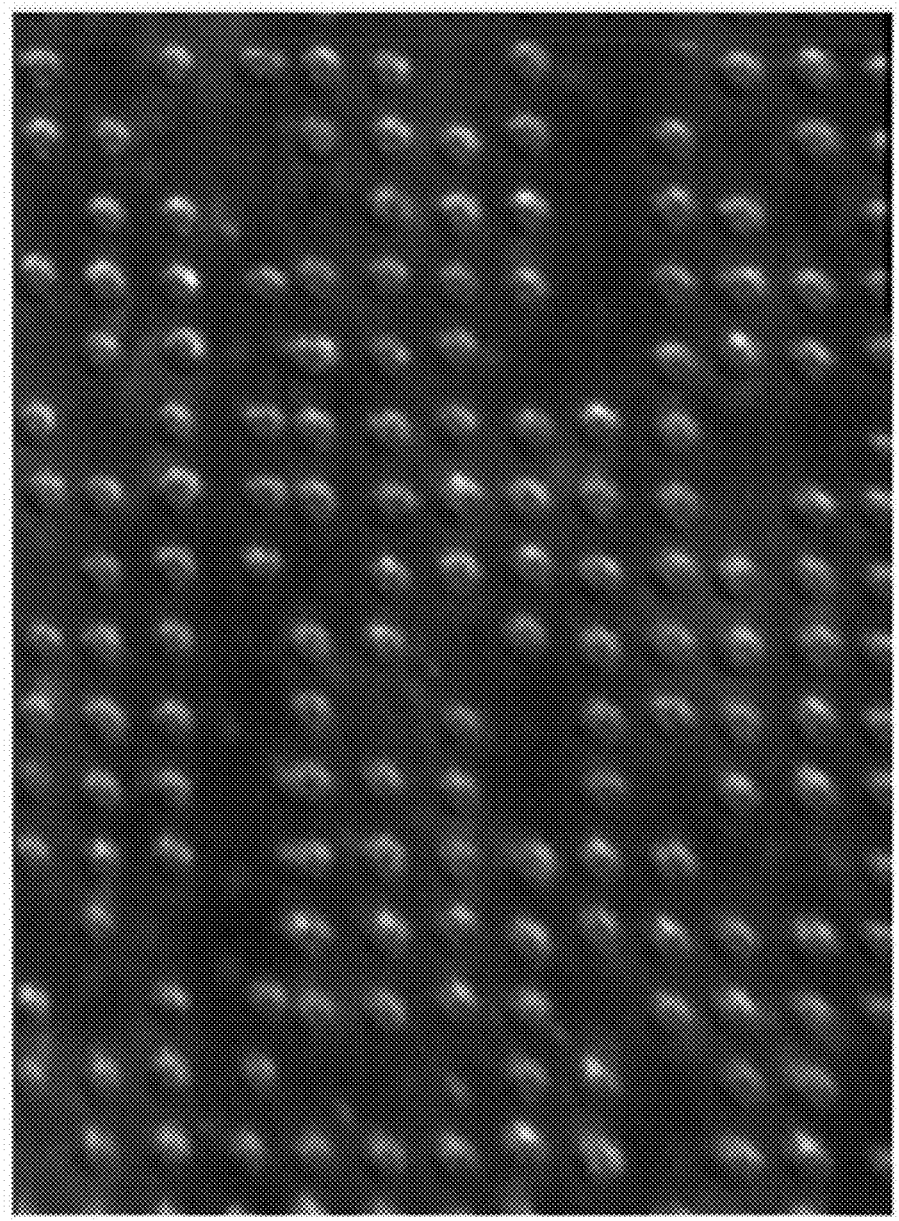
FIG. 6B is a digital image of the printed patter of FIG. 6A.

Referring to FIG. 6B, an image of a printed pattern according to the present disclosure is provided. This image was captured immediately after printing.

Figure 7:
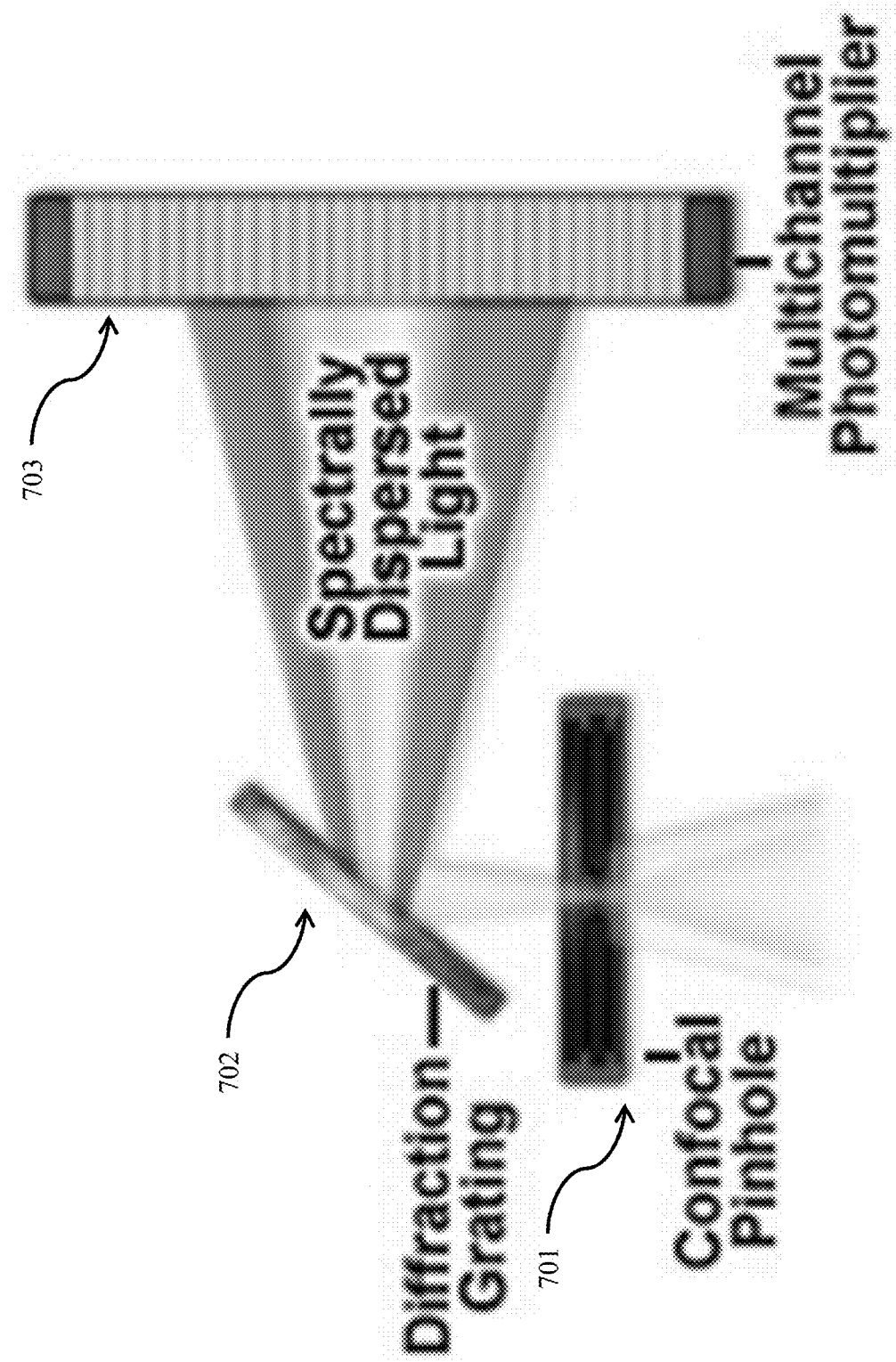
FIG. 7 is a schematic view of an exemplary reader according to embodiments of the present disclosure.
Figure 8A:
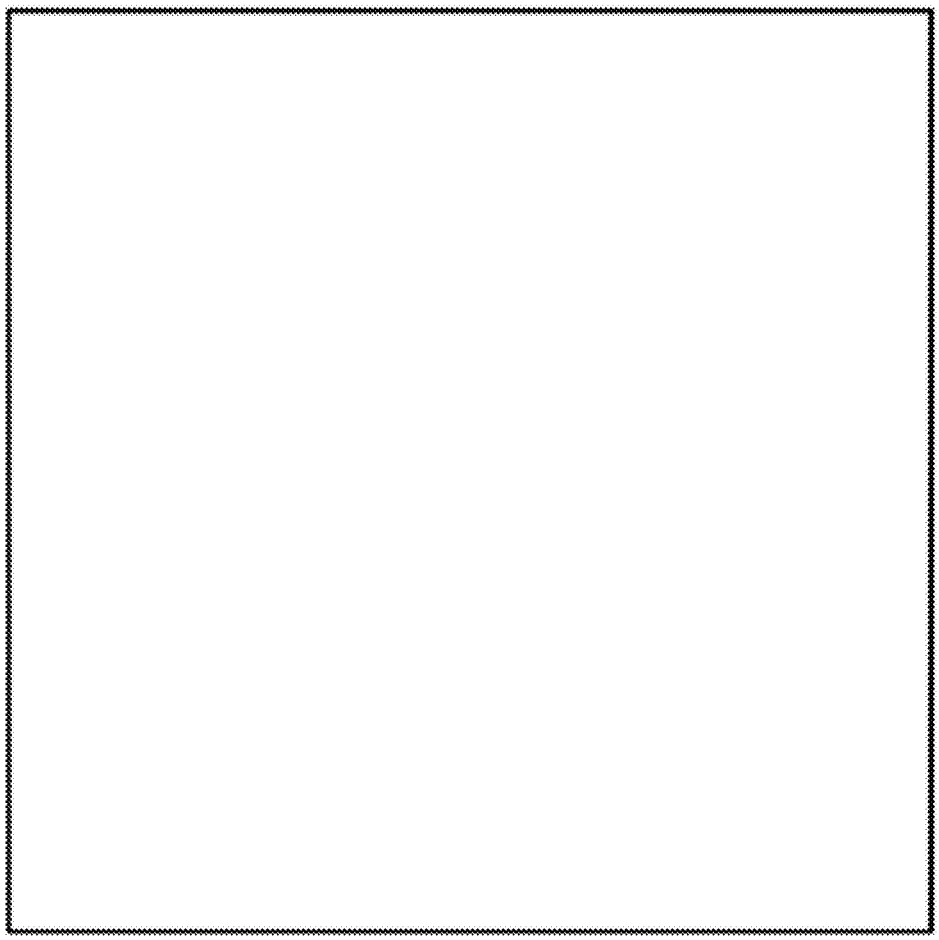
FIGS. 8A-H are digital images of the dye patterns for each of eight dyes encoding information according to embodiments of the present disclosure.
Figure 8B:
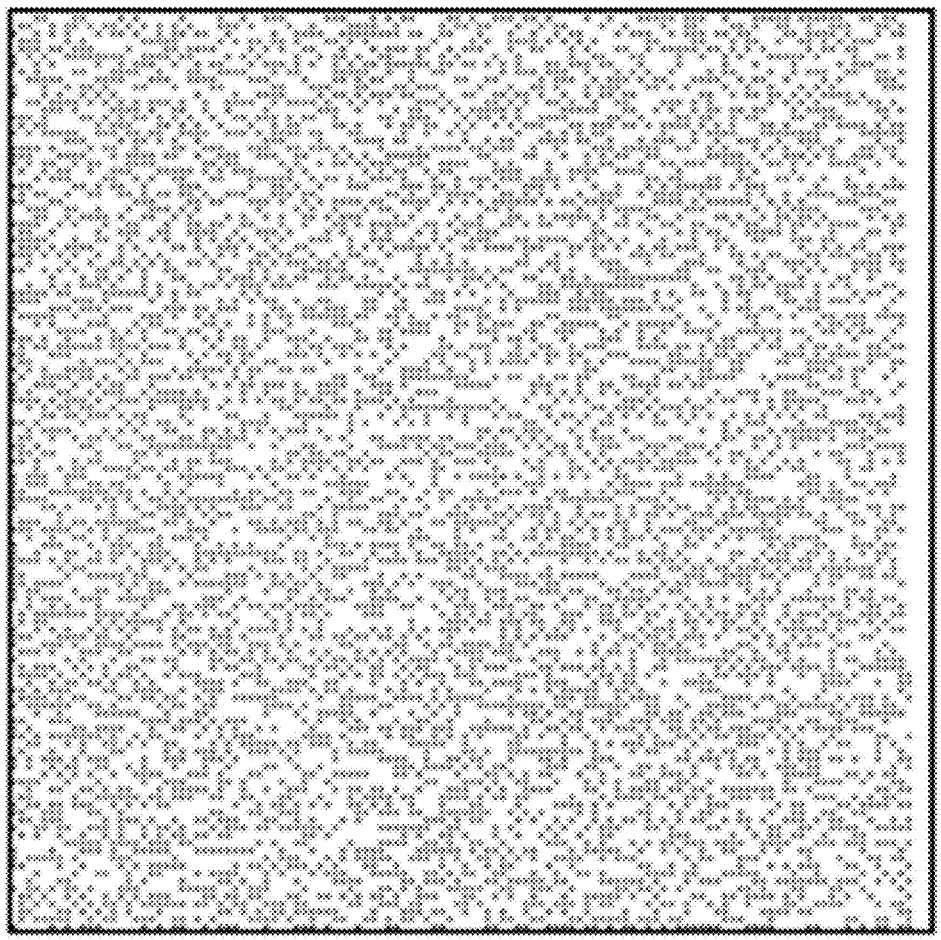
Figure 8C:
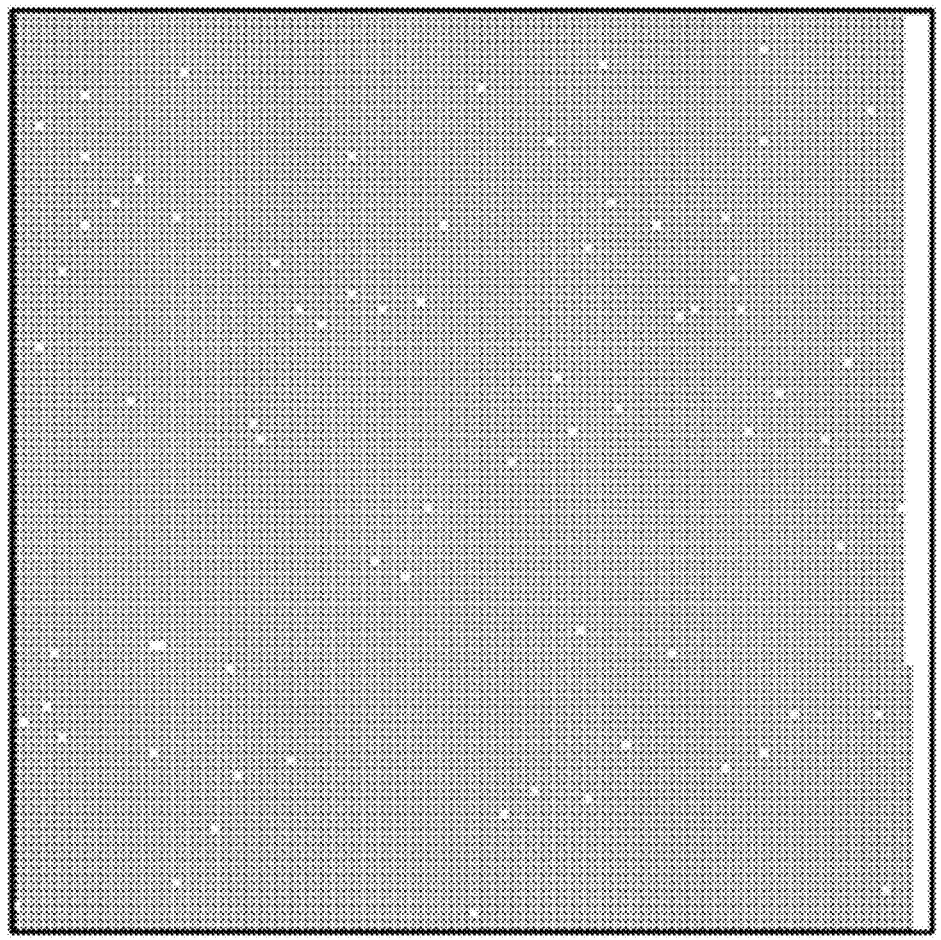
Figure 8D:
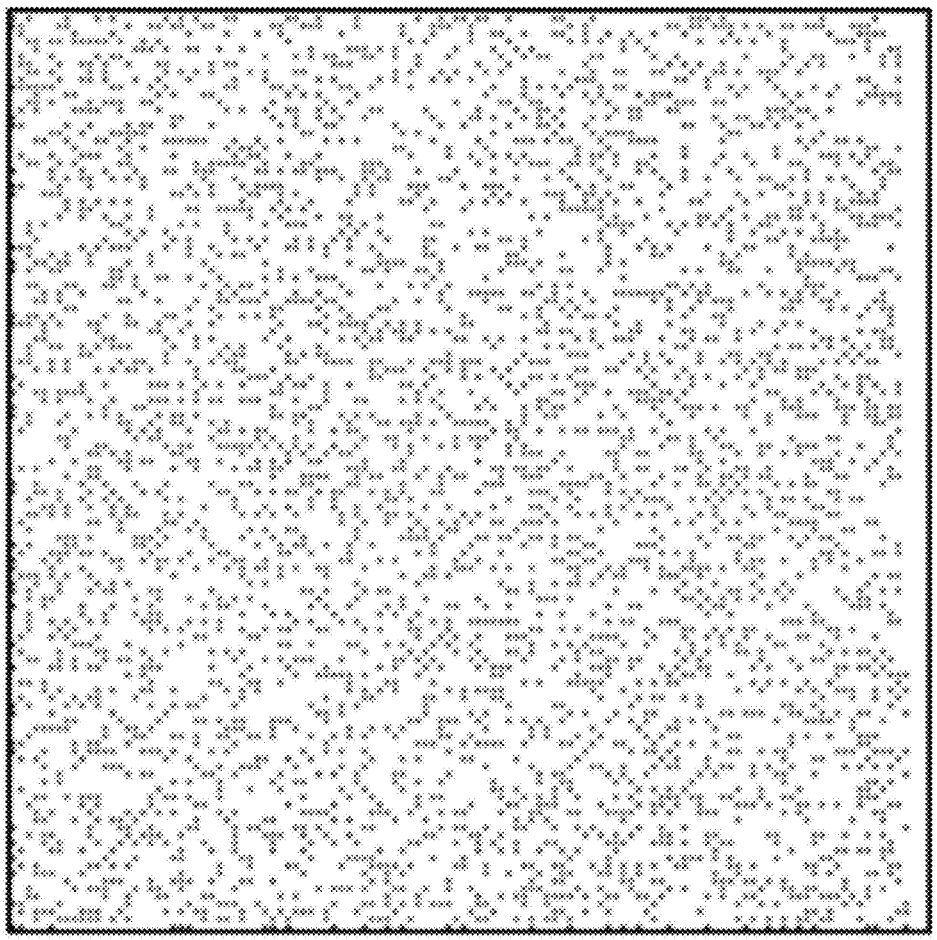
Figure 8E:
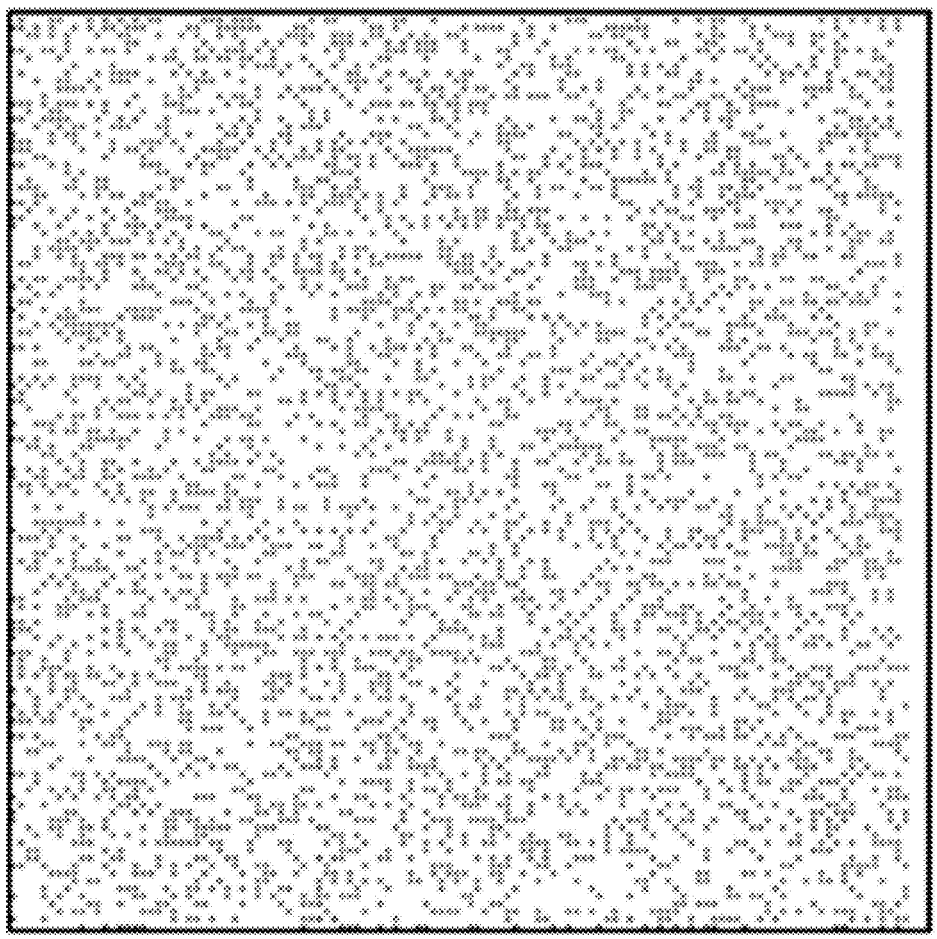
Figure 8F:
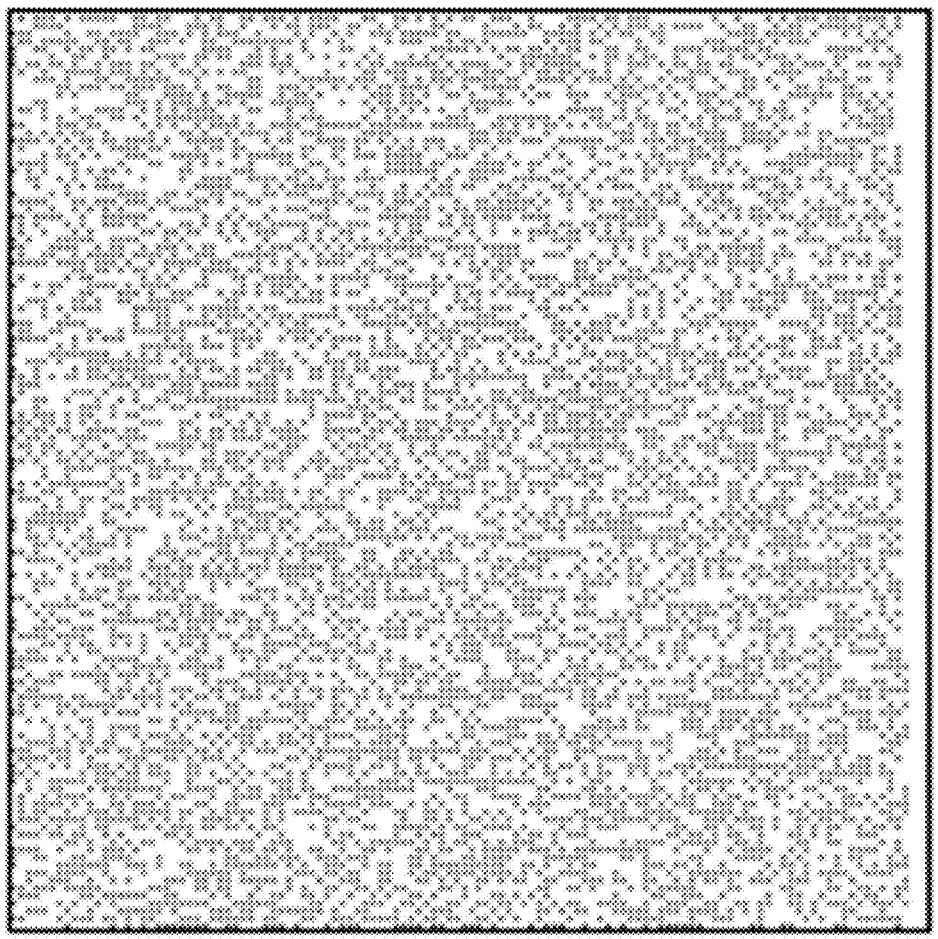
Figure 8G:
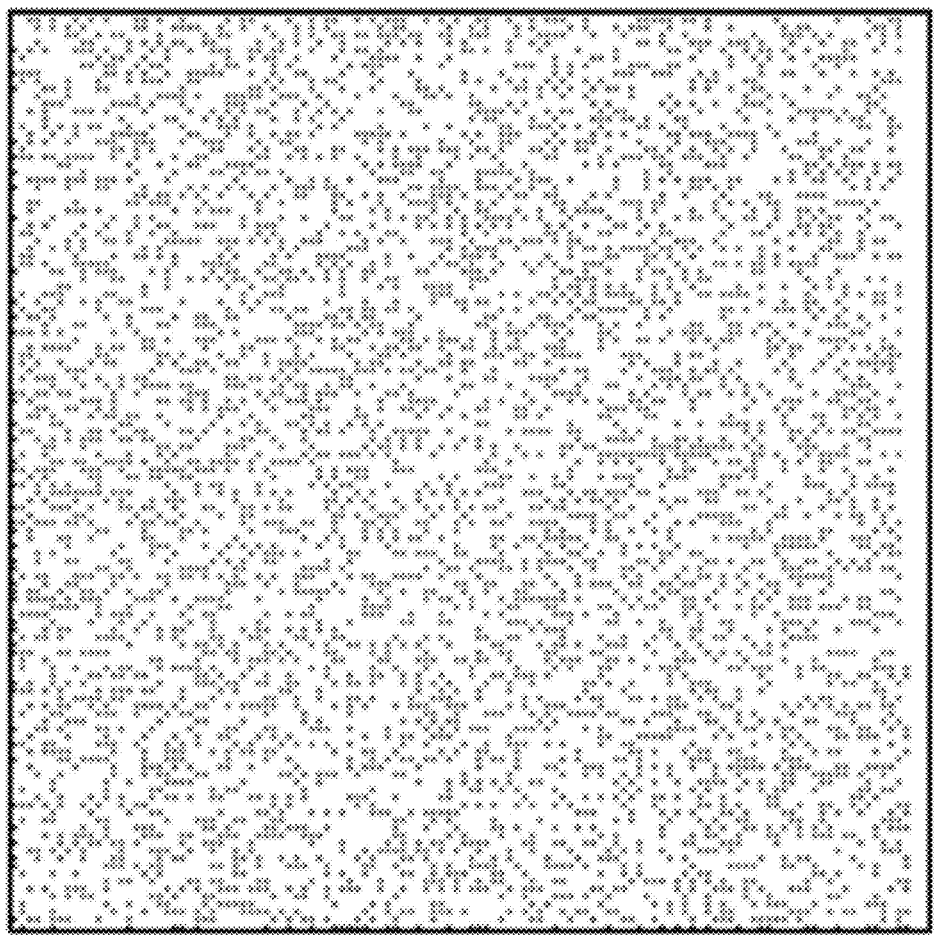
Figure 8H:
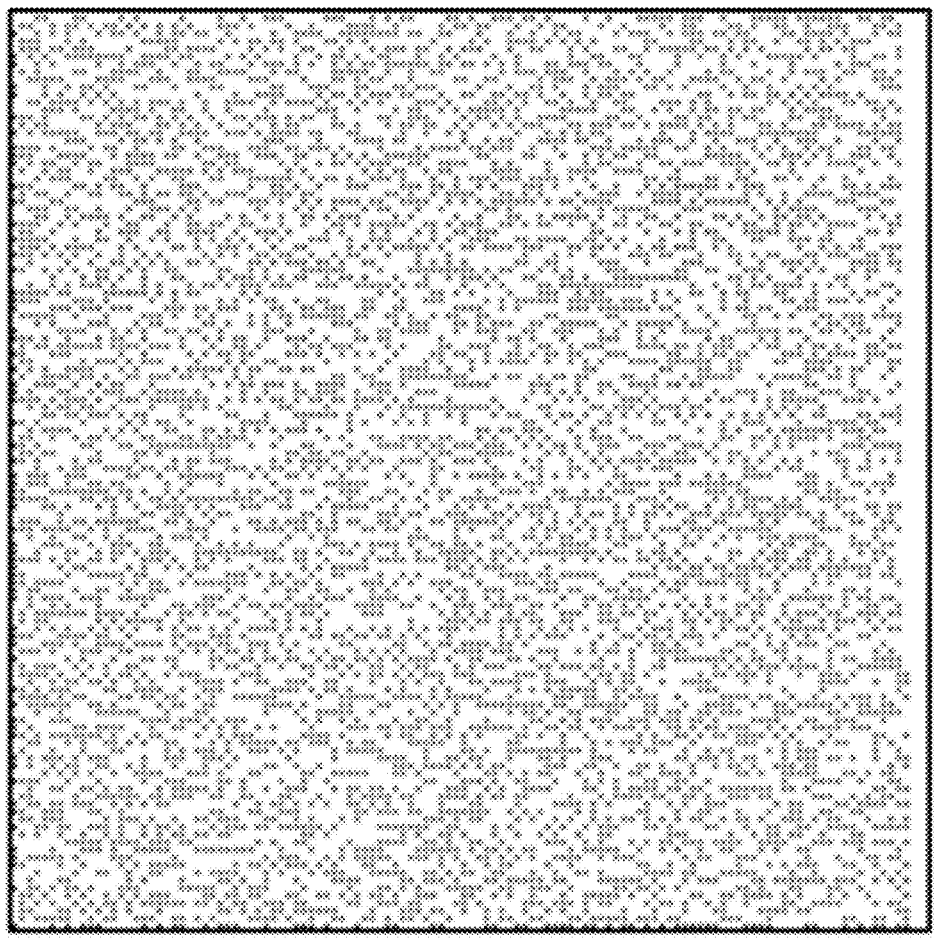

Referring to FIG. 7, a schematic view of an exemplary reader is provided. In various embodiments, a fluorescent detector capable of detecting multiple emissions with overlapping spectra is employed. Point illumination is employed, and a pinhole in an optically conjugate plane 701 in front of the detector is used to eliminate out-of-focus signal. As only light produced by fluorescence very close to the focal plane can be detected, the image's optical resolution is better than that of wide-field microscopes. In various embodiments, a diffraction grating 702 is used to spectrally disperse the light. The light intensity is then detected by a detector such as a multichannel photomultiplier 703, photomultiplier tube (PMT), or avalanche photodiode.

As set out above, an inkjet printer and a multichannel fluorescence detector enable a fast, higher density, and simple approach to storage of information for long time scales and at low cost using mixtures of fluorescent quantum dots.

Referring to FIGS. 8A-H, digital images are provided of the dye patterns for each of the eight dyes used in the above example.

Figure 9:
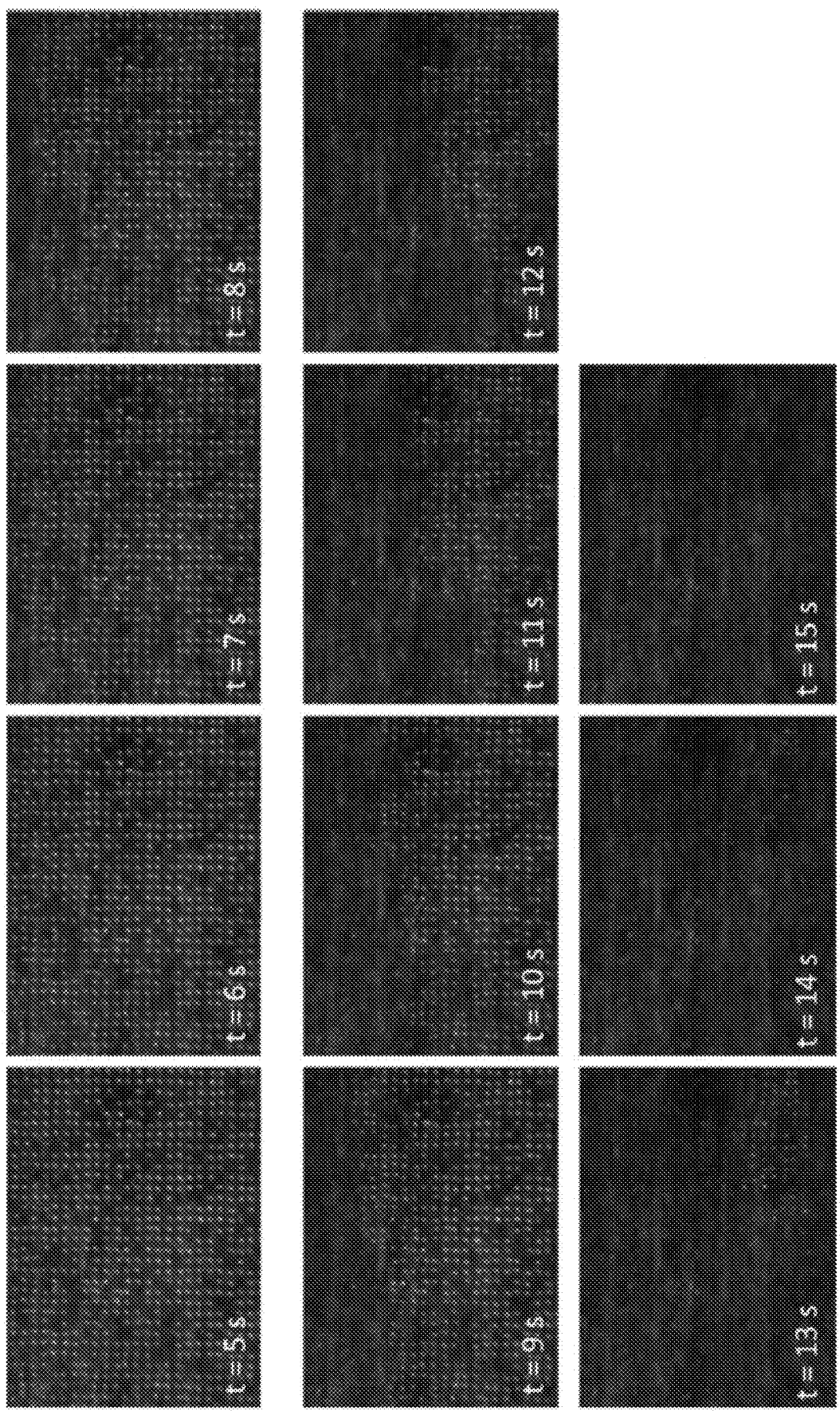
FIG. 9 is a time-series of images of an exemplary printed pattern according to embodiments of the present disclosure.

Referring to FIG. 9, a time-series of images of an exemplary pattern are provided. It will be observed that the printed droplet pattern disappears from the substrate surface over time due to absorption. Although not necessarily visible at visual wavelengths, the data remains readable by the methods described herein.

Figure 10:
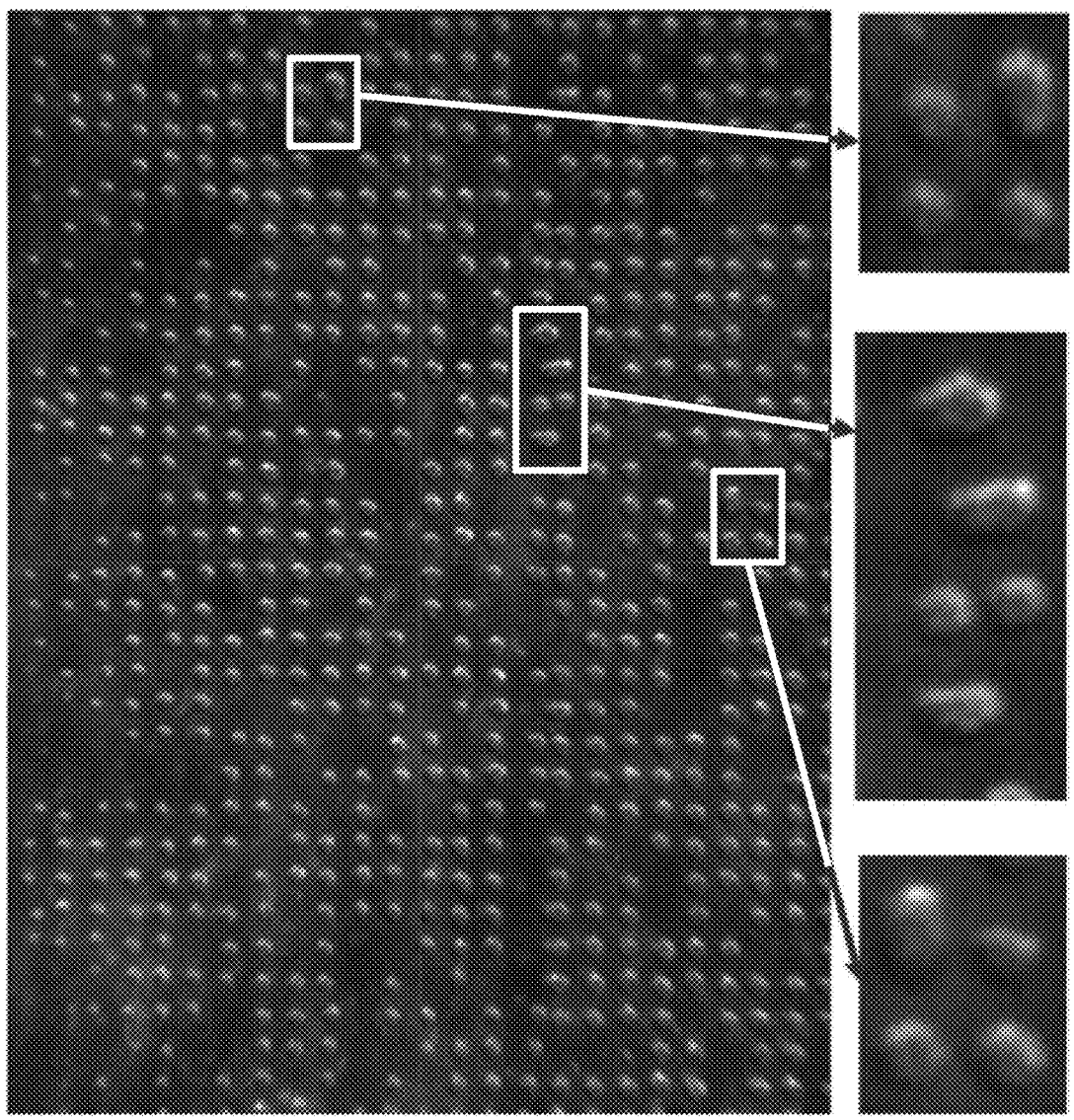
FIG. 10 is a digital image is provided of an exemplary pattern after multiple dyes have been deposited according to embodiments of the present disclosure.

Referring to FIG. 10, a digital image is provided of an exemplary pattern after multiple dyes have been deposited. In this example, there is slight misalignment between dyes when printing at 25 micron resolution. However, as set out above, the data remain readable despite this misalignment, allowing deposition using cost-effective and fast techniques such as ink jet printing.

Figure 11:
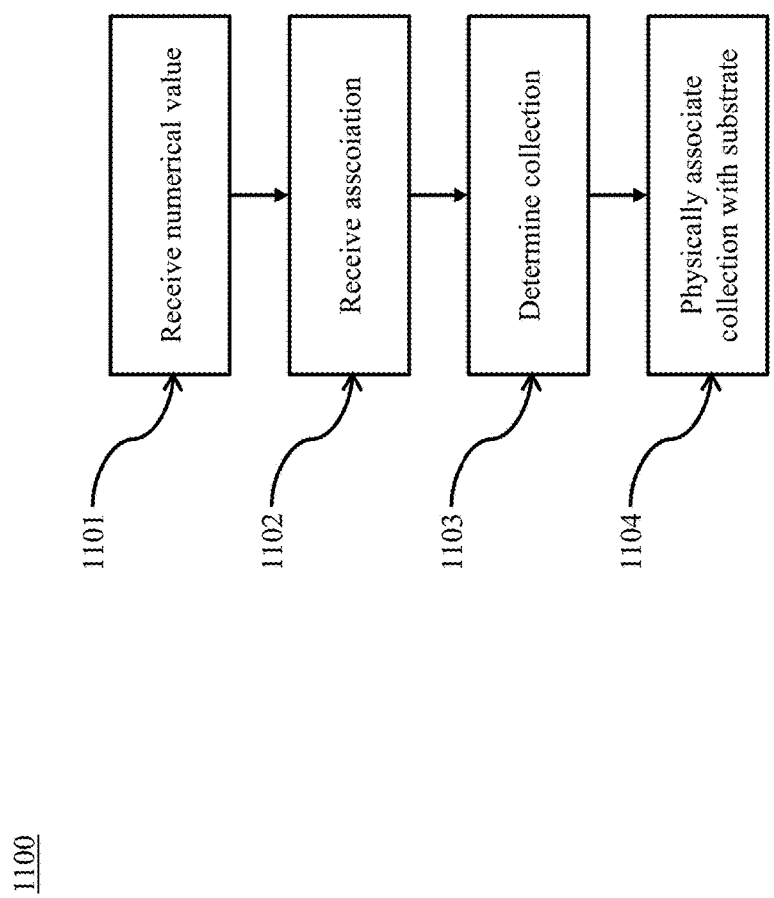
FIG. 11 is a flowchart illustrating a method for writing data according to embodiments of the present disclosure.

Referring to FIG. 11, a flowchart is provided illustrating a method for writing data according to embodiments of the present disclosure. At 1101, a numerical value is received, comprising a plurality of digits, each digit having a position. At 1102, a one-to-one association between a plurality of digit/position pairs and a set of unambiguously identifiable molecules is received. At 1103, a collection of molecules corresponding to the numerical value is determined. Determining the collection comprises: including in the collection the molecule associated with each position having the associated digit in the numerical value. At 1104, the molecules of the collection are physically associated with a substrate of the machine-readable medium at an addressable location thereon. Physically associating comprises linking to the substrate.

Figure 12:
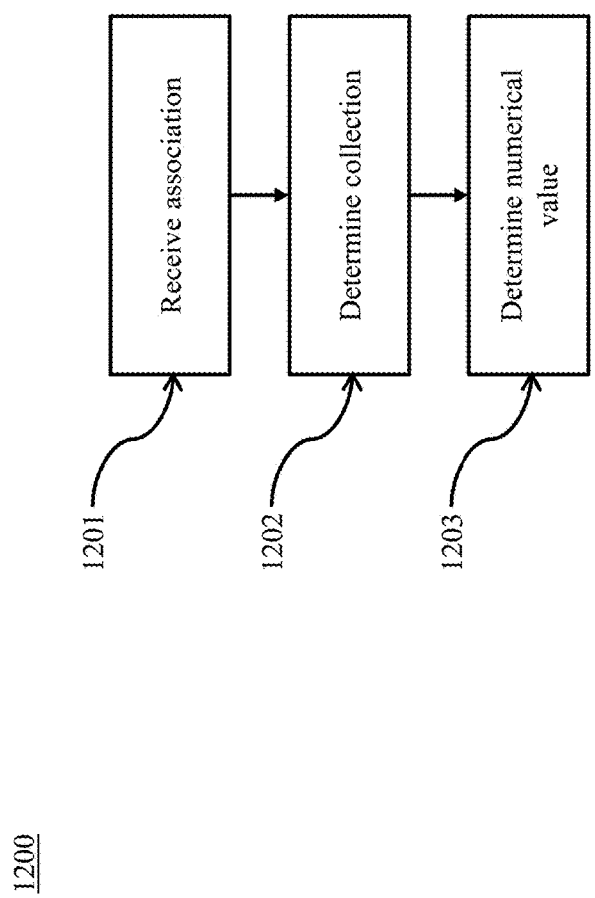
FIG. 12 is a flowchart illustrating a method for reading data according to embodiments of the present disclosure.

Referring to FIG. 12, a flowchart is provided illustrating a method for reading data according to embodiments of the present disclosure. At 1201, a one-to-one association between a plurality of digit/position pairs and a set of unambiguously identifiable molecules is received. At 1202, a collection of molecules physically associated with a substrate of the machine-readable medium at an addressable location thereon is determined. Each molecule in the collection is linked to the substrate at the respective addressable location. At 1203, a numerical value is determined from the collection of molecules. Determining the numerical value comprises: setting each position of the numerical value to the digit whose associated molecule is present in the collection.

Figure 13:
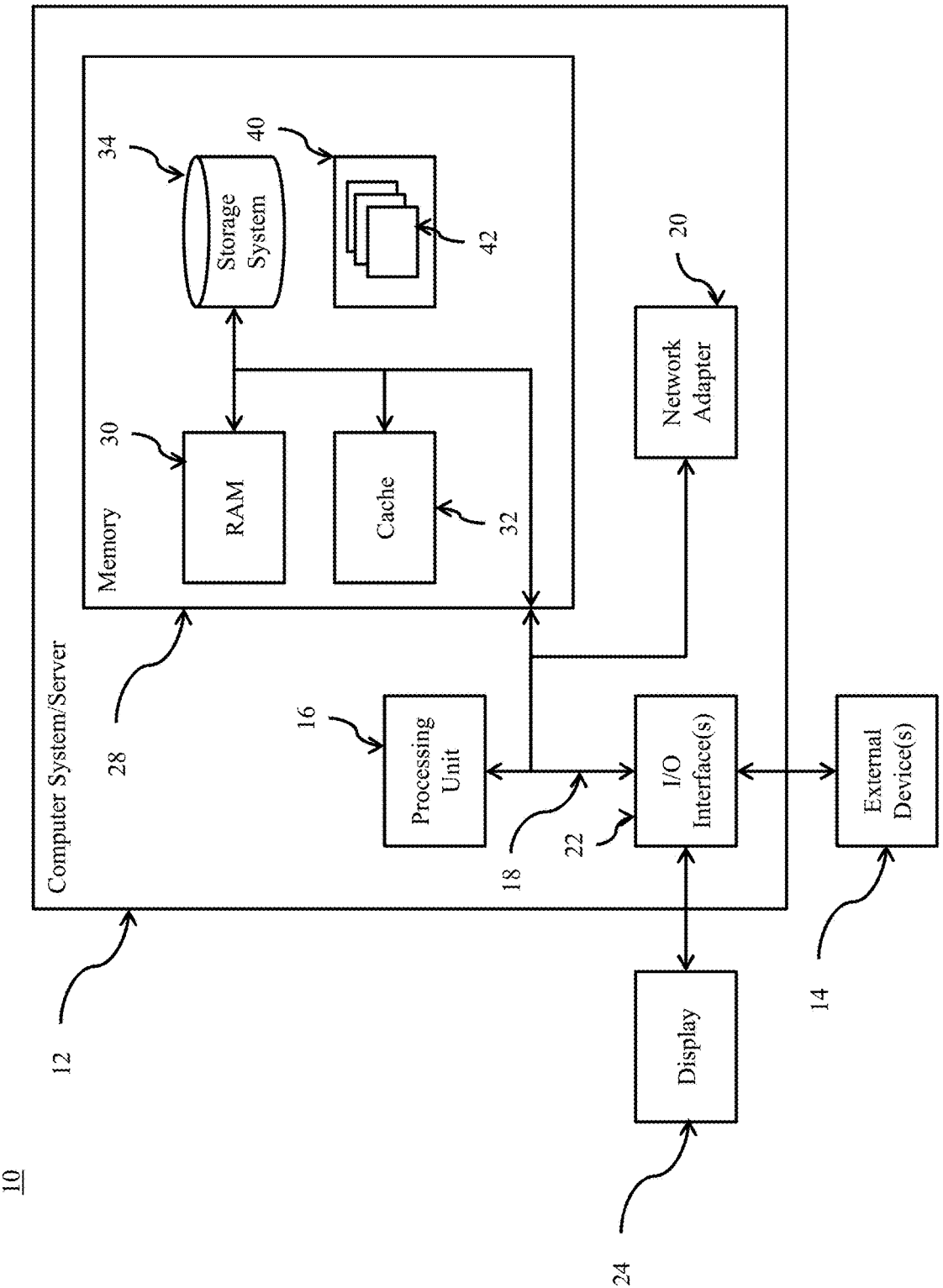
FIG. 13 is a schematic view of a computing node according to embodiments of the present disclosure.

Referring now to FIG. 13, a schematic of an example of a computing node is shown. Computing node 10 is only one example of a suitable computing node and is not intended to suggest any limitation as to the scope of use or functionality of embodiments described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 13, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus, Peripheral Component Interconnect Express (PCIe), and Advanced Microcontroller Bus Architecture (AMBA).

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

In various example embodiments the present invention can be defined as following numbered examples.

1. A machine-readable medium comprising: a substrate having an array of addressable locations thereon, each addressable location adapted to be physically associated with a collection of non-polymeric molecules, wherein the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position.

2. A machine-readable medium comprising a substrate having an array of addressable locations thereon, each addressable location adapted to be physically associated with a collection of molecules, wherein each molecule in the collection is a sequence-independent polymer, and wherein the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position.

3. The machine-readable medium of 1 or 2, wherein each molecule of the set of unambiguously identifiable molecules is associated with a binary digit.

4. The machine-readable medium of 1 or 2, wherein the numerical value has a radix and a predetermined number of positions.

5. The machine-readable medium of 4, wherein the numerical value is a binary value having a predetermined number, N, of bits.

6. The machine-readable medium of 6, wherein the numerical value is a binary value having 32 bits.

7. The machine-readable medium of 5, wherein each collection encodes a bit string.

8. The machine-readable medium of 7, wherein the bit string encodes an ASCII value.

9. The machine-readable medium of any one of 1-8, wherein each molecule in the set is identifiable by a physical property.

10. The machine-readable medium of 9, wherein the physical property is a mass-to-charge ratio.

11. The machine-readable medium of any one of 1-10, wherein each molecule in the collection is linked to the substrate at the respective addressable location.

12. The machine-readable medium of 2 or any one of 3-10, wherein each molecule in the set is a polymer or an oligomer.

13. The machine-readable medium of 12, wherein each molecule is an oligopeptide.

14. The machine-readable medium of 13, wherein each molecule includes a $N^\epsilon$, $N^\epsilon$, $N^\epsilon$-trimethyl lysine-cysteine ($K^{(Me3)}C$) dipeptide at its C-terminus.

15. The machine-readable medium of 1 or 2, wherein the numerical value is a binary value having 32 bits; and the set of molecules includes the oligopeptides represented by the following amino acid sequences: Ac-AK(me3)C, Ac-(abu)K(me3)C, Ac-VK(me3)C, Ac-GGK(me3)C, Ac-GVK(me3)C, Ac-GLK(me3)C, Ac-ALK(me3)C, Ac-GFK(me3)C, Ac-GVGK(me3)C, Ac-GLGK(me3)C, Ac-GAGGK(me3)C, Ac-GL(abu)K(me3)C, Ac-GFGK(me3)C, Ac-GRGK(me3)C, Ac-GPAGK(me3)C, Ac-AYGK(me3)C, Ac-GPFK(me3)C, Ac-GVVGK(me3)C, Ac-G(abu)FGK(me3)C, Ac-GVFGK(me3)C, Ac-GVYGK(me3)C, Ac-GARGGK(me3)C, Ac-GAVV(abu)K(me3)C, Ac-GFYGK(me3)C, Ac-GYYGK(me3)C, Ac-GYYAK(me3)C, Ac-GPYFK(me3)C, Ac-GRGFGK(me3)C, Ac-GYFGGK(me3)C, Ac-GYYGGK(me3)C, Ac-AYYGGK(me3)C, and Ac-GYY(abu)GK(me3)C, wherein each Ac is an acetyl and each Abu is a 2-aminobutyric acid.

16. A method of writing data to a machine-readable medium, the method comprising receiving a binary value comprising a plurality of bits, each bit having a position; receiving a one-to-one association between a plurality of bit positions and a set of unambiguously identifiable molecules; determining a collection of molecules corresponding to the binary value, wherein determining the collection comprises: including in the collection the molecule associated with each position in which the bit has a value of 1; and omitting the molecule associated with each position in which the bit has a value of 0; physically associating the molecules of the collection with a substrate of the machine-readable medium at an addressable location thereon.

17. A method of reading data from a machine-readable medium, the method comprising receiving a one-to-one association between each of a plurality of bit positions and a set of unambiguously identifiable molecules; determining a collection of molecules physically associated to a substrate of the machine-readable medium at an addressable location thereon; determining a binary value from the collection of molecules, wherein determining the binary value comprises: setting to 1 the bit at the position in the binary value for which its associated molecule is present in the collection and setting to 0 each bit at the position of the binary value for which its associated molecule is not present in the collection.

18. A method of writing data to a machine-readable medium, the method comprising receiving a numerical value comprising a plurality of digits, each digit having a position; receiving a one-to-one association between a plurality of digit/position pairs and a set of unambiguously identifiable molecules; determining a collection of molecules corresponding to the numerical value, wherein determining the collection comprises: including in the collection the molecule associated with each position having the associated digit in the numerical value; physically associating the molecules of the collection with a substrate of the machine-readable medium at an addressable location thereon.

19. A method of reading data from a machine-readable medium, the method comprising receiving a one-to-one association between a plurality of digit/position pairs and a set of unambiguously identifiable molecules; determining a collection of molecules physically associated with a substrate of the machine-readable medium at an addressable location thereon; determining a numerical value from the collection of molecules, wherein determining the numerical value comprises: setting each position of the numerical value to the digit whose associated molecule is present in the collection.

20. The method of any one of 16-19, wherein receiving the association comprises reading a lookup table.

21. The method of any one of 16-19, wherein the numerical value is a binary value having a predetermined number, N, of bits.

22. The method of 21, wherein the numerical value is a binary value having 32 bits.

23. The method of any one of 16-22, wherein each collection encodes a bit string.

24. The method of 23, wherein the bit string encodes an ASCII value.

25. The method of any one of 16-24, wherein each molecule in the set is identifiable by a physical property.

26. The method of 25, wherein each molecule in the set is identifiable by a mass-to-charge ratio.

27. The method of any one of 16-26, wherein each molecule in the collection is linked to the substrate at the respective addressable location.

28. The method of 17 or 19, wherein determining the collection of molecules comprises determining a physical property of the molecules in the collection.

29. The method of 17 or 19, wherein determining the collection of molecules comprises determining the mass-to-charge ratio of the molecules in the collection.

30. The method of any one of 16-29, wherein the numerical value is a binary value having 32 bits; and the set of molecules includes the oligopeptides represented by the following amino acid sequences: Ac-AK(me3)C, Ac-(abu)K(me3)C, Ac-VK(me3)C, Ac-GGK(me3)C, Ac-GVK(me3)C, Ac-GLK(me3)C, Ac-ALK(me3)C, Ac-GFK(me3)C, Ac-GVGK(me3)C, Ac-GLGK(me3)C, Ac-GAGGK(me3)C, Ac-GL(abu)K(me3)C, Ac-GFGK(me3)C, Ac-GRGK(me3)C, Ac-GPAGK(me3)C, Ac-AYGK(me3)C, Ac-GPFK(me3)C, Ac-GVVGK(me3)C, Ac-G(abu)FGK(me3)C, Ac-GVFGK(me3)C, Ac-GVYGK(me3)C, Ac-GARGGK(me3)C, Ac-GAVV(abu)K(me3)C, Ac-GFYGK(me3)C, Ac-GYYGK(me3)C, Ac-GYYAK(me3)C, Ac-GPYFK(me3)C, Ac-GRGFGK(me3)C, Ac-GYFGGK(me3)C, Ac-GYYGGK(me3)C, Ac-AYYGGK(me3)C, and Ac-GYY(abu)GK(me3)C, wherein each Ac is an acetyl and each Abu is a 2-aminobutyric acid.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A machine-readable medium comprising:
a substrate having an array of addressable locations thereon, each addressable location adapted to be physically associated with a collection of non-polymeric molecules,
wherein the molecules in each collection are selected from a set of unambiguously identifiable molecules, each molecule uniquely associated with a predetermined position in a numerical value, wherein the presence of the molecule in the collection indicates a predetermined digit at the associated position and the absence of said molecule in the collection indicates a zero at said associated position, and
further wherein each molecule in the collection is linked to the substrate at the respective addressable location.

2. The machine-readable medium of claim 1, wherein each molecule of the set of unambiguously identifiable molecules is associated with a binary digit.

3. The machine-readable medium of claim 1, wherein the numerical value has a radix and a predetermined number of positions.

4. The machine-readable medium of claim 3, wherein the numerical value is a binary value having a predetermined number, N, of bits.

5. The machine-readable medium of claim 4, wherein each collection encodes a bit string.

6. The machine-readable medium of claim 5, wherein the bit string encodes an ASCII value.

7. The machine-readable medium of claim 1, wherein each molecule in the set is identifiable by a physical property.

8. The machine-readable medium of claim 7, wherein the physical property is a fluorescent emission wavelength.

9. The machine-readable medium of claim 8, wherein each molecule in the set comprises a quantum dot.

10. The machine-readable medium of claim 9, wherein at least one molecule in the set comprises lead sulfide, lead selenide, cadmium selenide, cadmium sulfide, cadmium telluride, indium arsenide, indium phosphide, zinc selenide, or zinc sulfide.

11. The machine-readable medium of claim 9, wherein each molecule in the collection is linked to the substrate by an amide bond.

12. The machine-readable medium of claim 11, wherein the substrate comprises an epoxy resin.

13. The machine-readable medium of claim 7, wherein the physical property is a mass-to-charge ratio.

14. The machine-readable medium of claim 1, wherein:
the numerical value is a binary value having 32 bits; and
the set of molecules comprises the oligopeptides represented by the following amino acid sequences: Ac-AK(me3)C, Ac-(abu)K(me3)C, Ac-VK(me3)C, Ac-GGK(me3)C (SEQ ID NO: 1), Ac-GVK(me3)C (SEQ ID NO: 2), Ac-GLK(me3)C (SEQ ID NO: 3), Ac-ALK(me3)C (SEQ ID NO: 4), Ac-GFK(me3)C (SEQ ID NO: 5), Ac-GVGK(me3)C (SEQ ID NO: 6), Ac-GLGK(me3)C (SEQ ID NO: 7), Ac-GAGGK(me3)C (SEQ ID NO: 8), Ac-GL(abu)K(me3)C (SEQ ID NO: 9), Ac-GFGK(me3)C (SEQ ID NO: 10), Ac-GRGK(me3)C (SEQ ID NO: 11), Ac-GPAGK(me3)C (SEQ ID NO: 12), Ac-AYGK(me3)C (SEQ ID NO: 13), Ac-GPFK(me3)C (SEQ ID NO: 14), Ac-GVVGK(me3)C (SEQ ID NO: 15), Ac-G(abu)FGK(me3)C (SEQ ID NO: 16), Ac-GVFGK(me3)C (SEQ ID NO: 17), Ac-GVYGK(me3)C (SEQ ID NO: 18), Ac-GARGGK(me3)C (SEQ ID NO: 19), Ac-GAVV(abu)K(me3)C (SEQ ID NO: 20), Ac-GFYGK(me3)C (SEQ ID NO: 21), Ac-GYYGK(me3)C (SEQ ID NO: 22), Ac-GYYAK(me3)C (SEQ ID NO: 23), Ac-GPYFK(me3)C (SEQ ID NO: 24), Ac-GRGFGK(me3)C (SEQ ID NO: 25), Ac-GYFGGK(me3)C (SEQ ID NO: 26), Ac-GYYGGK(me3)C (SEQ ID NO: 27), Ac-AYYGGK(me3)C (SEQ ID NO: 28), and Ac-GYY(abu)GK(me3)C (SEQ ID NO: 29), wherein each Ac is an acetyl and each Abu is a 2-aminobutyric acid.

* * * * *

SEQUENCE LISTING

```
<160> NUMBER OF SEQ ID NOS: 53

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (2)..(2)
<223> OTHER INFORMATION: METHYLATION

<400> SEQUENCE: 1

Gly Gly Lys Cys
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: METHYLATION

<400> SEQUENCE: 2
```

```
Gly Val Lys Cys
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: METHYLATION

<400> SEQUENCE: 3

Gly Leu Lys Cys
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: METHYLATION

<400> SEQUENCE: 4

Ala Leu Lys Cys
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (3)..(3)
<223> OTHER INFORMATION: METHYLATION

<400> SEQUENCE: 5

Gly Phe Lys Cys
1

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 6

Gly Val Gly Lys Cys
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 7

Gly Leu Gly Lys Cys
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 8

Gly Ala Gly Gly Lys Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (3)..(3)
<223> OTHER INFORMATION: Xaa = Abu
<220> FEATURE:
<221> NAME/KEY: MOD_RES
<222> LOCATION: (4)..(4)
<223> OTHER INFORMATION: METHYLATION

<400> SEQUENCE: 9
```

```
Gly Leu Xaa Lys Cys
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 10

Gly Phe Gly Lys Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 11

Gly Arg Gly Lys Cys
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 12

Gly Pro Ala Gly Lys Cys
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 13

Ala Tyr Gly Lys Cys
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: METHYLATION

<400> SEQUENCE: 14

Gly Pro Phe Lys Cys
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (1)..(1)
<223> OTHER INFORMATION: METHYLATION

<400> SEQUENCE: 15

Gly Val Val Gly Lys Cys
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (2)..(2)
<223> OTHER INFORMATION: Xaa = Abu
<220> FEATURE:
<221> NAME/KEY: MOD_RES
<222> LOCATION: (5)..(5)
<223> OTHER INFORMATION: METHYLATION

<400> SEQUENCE: 16
```

```
Gly Xaa Phe Gly Lys Cys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 17

Gly Val Phe Gly Lys Cys
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 18

Gly Val Tyr Gly Lys Cys
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION

<400> SEQUENCE: 19

Gly Ala Arg Gly Gly Lys Cys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: VARIANT
<222> LOCATION: (5)..(5)
<223> OTHER INFORMATION: Xaa = abu
<220> FEATURE:
<221> NAME/KEY: MOD_RES
<222> LOCATION: (6)..(6)
<223> OTHER INFORMATION: METHYLATION

<400> SEQUENCE: 20

Gly Ala Val Val Xaa Lys Cys
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 21

Gly Phe Tyr Gly Lys Cys
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 22

Gly Tyr Tyr Gly Lys Cys
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 23
```

```
Gly Tyr Tyr Ala Lys Cys
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (5)..(5)
<223> OTHER INFORMATION: METHYLATION

<400> SEQUENCE: 24

Gly Pro Tyr Phe Lys Cys
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION

<400> SEQUENCE: 25

Gly Arg Gly Phe Gly Lys Cys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION

<400> SEQUENCE: 26

Gly Tyr Phe Gly Gly Lys Cys
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION

<400> SEQUENCE: 27

Gly Tyr Tyr Gly Gly Lys Cys
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: METHYLATION

<400> SEQUENCE: 28

Ala Tyr Tyr Gly Gly Lys Cys
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: VARIANT
<222> LOCATION: (4)..(4)
<223> OTHER INFORMATION: Xaa = Abu
<220> FEATURE:
<221> NAME/KEY: MOD_RES
<222> LOCATION: (6)..(6)
<223> OTHER INFORMATION: METHYLATION

<400> SEQUENCE: 29

Gly Tyr Tyr Xaa Gly Lys Cys
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Trp Asp Asp Asp Phe
1               5

<210> SEQ ID NO 31
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 31

Trp Asp Asp Asp Leu
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Trp Asp Asp Asp Val
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Asp Asp Asp Pro
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: VARIANT
<222> LOCATION: (5)..(5)
<223> OTHER INFORMATION: Xaa = Abu

<400> SEQUENCE: 34

Trp Asp Asp Asp Xaa
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Trp Asp Asp Asp Ala
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36
```

```
Trp Asp Asp Gly
1               5

<210> SEQ ID NO 37
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Asp Asp Asp
1

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Trp Asp Asp Asn
1

<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Trp Asp Asp Lys
1

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Trp Asp Asp Asp Asn
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Asp Asp Asp Lys
1               5

<210> SEQ ID NO 42
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 42

Trp Asp Asp Asp Asn
1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Trp Asp Asp Asp Asp Lys
1               5

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Trp Asp Asp Asp Asp Asp Asn
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Trp Asp Asp Asp Asp Asp Lys
1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Trp Asp Asp Asp Asp Asp Asp Asn
1               5

<210> SEQ ID NO 47
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Trp Asp Asp Asp Asp Asp Asp Lys
1               5
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Trp Asp Asp Asp Asp Asp Asp Asp Asn
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Asp Asp Asp Asp Asp Asp Asp Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Trp Asp Asp Asp Asp Asp Asp Asp Asp Asn
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Trp Asp Asp Asp Asp Asp Asp Asp Asp Lys
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Trp Asp Asp Asp Asp Asp Asp Asp Asp Asp Asn
1               5                   10

```
<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Trp Asp Asp Asp Asp Asp Asp Asp Asp Asp Lys
1               5                   10
```